US008283616B2

(12) United States Patent
Novak

(10) Patent No.: US 8,283,616 B2
(45) Date of Patent: Oct. 9, 2012

(54) METHOD AND APPARATUS FOR MICROWAVE DISSOCIATION OF ORGANIC COMPOUNDS

(76) Inventor: John F. Novak, Fredericktown, OH (US)

( * ) Notice: Subject to any disclaimer, the term of this patent is extended or adjusted under 35 U.S.C. 154(b) by 0 days.

(21) Appl. No.: 13/043,074

(22) Filed: Mar. 8, 2011

(65) Prior Publication Data

US 2011/0215092 A1 Sep. 8, 2011

Related U.S. Application Data

(60) Provisional application No. 61/311,432, filed on Mar. 8, 2010.

(51) Int. Cl.
*H05B 6/70* (2006.01)
*C07C 1/00* (2006.01)

(52) U.S. Cl. .................................. 219/679; 204/157.15

(58) Field of Classification Search .................. 219/679, 219/695, 696; 204/157.15, 157.6, 157.4, 204/157.43; 422/186; 210/748.01, 748.07; 201/3, 10; 407/116
See application file for complete search history.

(56) References Cited

U.S. PATENT DOCUMENTS

| | | | | |
|---|---|---|---|---|
| 4,776,936 | A | 10/1988 | Smith et al. | |
| 5,406,237 | A | 4/1995 | Ravas et al. | |
| 7,927,465 | B2 * | 4/2011 | Novak | 204/157.15 |
| 2007/0102279 | A1 | 5/2007 | Novak | |
| 2007/0131591 | A1 * | 6/2007 | Pringle | 208/402 |
| 2008/0179177 | A1 | 7/2008 | Cha | |

OTHER PUBLICATIONS

International Search Report for PCT/US2011/027541 dated May 12, 2011.
Written Opinion for PCT/US2011/027541 dated May 12, 2011.

* cited by examiner

*Primary Examiner* — Quang Van
(74) *Attorney, Agent, or Firm* — Hahn Loeser & Parks LLP

(57) ABSTRACT

The invention describes a process for reducing an organic-containing material into lower molecular weight gaseous hydrocarbons, liquid hydrocarbons and solid carbon constituents, by using out-of-phase microwaves which enter the applicator through at least one applicator diffuser matrix. The matrix includes essentially parallel beveled entry channels.

26 Claims, 15 Drawing Sheets

METHOD AND APPARATUS FOR MICROWAVE DISSOCIATION OF ORGANIC COMPOUNDS

CROSS-REFERENCE TO RELATED APPLICATIONS

This application claims priority to provisional U.S. patent application Ser. No. 61/311,432 filed 8 Mar. 2010, the provisional application hereinby incorporated by reference.

TECHNICAL FIELD

The invention described herein pertains generally to a more efficient and cost-effective method and apparatus for: (1) coupling of microwave energy from a microwave generator to an applicator; (2) matching the applied microwave energy from the microwave generator to the type and volume of material within the applicator; (3) diffusion of high power density microwave energy volumetrically throughout the applicator; (4) transfer of energy volumetrically to the applicator material via high-speed microwave absorption and thermally-conductive techniques; and (5) reduced energy consumption.

The improvements described in this process result in improved microwave absorption within the material in the applicator, resulting in more even temperature distribution throughout the applicator, leading to more rapid molecular breakdown of organic compounds to fuels including syngas, fuel oil, and carbon. Alternately, this invention also rapidly and safely dissociates hazardous organic materials into harmless byproducts.

The invention described herein pertains generally to a the following reactions: depropagating polymer-based materials, e.g., plastics, asphalt roofing shingles and rubber, including crosslinked plastics and rubber-based polymers, including cross-linked rubbers such as sulfur-based crosslinks, as used in tires; decrosslinking and at least partially depolymerizing product without combustion, including computer waste and poly-chlorinated biphenyl (PCB), poly-aromatic hydrocarbon (PAH), and/or hexachlorinated benzene (HCB)-laden material; drying and sterilizing as well as volumetric reduction of materials without an external heat source, including municipal solid waste (MSW), medical waste, and construction waste; recovery of shale oil from rock formations; and reduction of bituminous coal to carbon, hydrocarbon gases and ash.

BACKGROUND OF THE INVENTION

In the field of petrochemicals, escalating energy costs for oil, natural gas, liquefied petroleum gas (LPG), and liquefied natural gas (LNG) are of increasing concern to those involved in the processing of organic materials, chemicals, and petroleum products. With the inherent aging of the facilities, coupled with the ever-escalating energy and capital equipment costs, refurbishment and replacement costs of these plants becomes increasingly difficult to justify. Many efforts have been expended in those applications described in the Technical Field to produce directly useable fuels from scrap tires or plastics without further treatment, substantially improve throughput, increase operating efficiency, or reduce energy consumption, but have failed due to economic or technical reasons. The present invention achieves all of these objectives through the direct application of high-density microwave energy to various organic materials, while simplifying the process methods and apparatus.

This invention addresses the problems of accumulation of waste products including tires, plastics, roofing shingles, construction debris in ever-decreasing space in landfills. In the United States, as of the filing date of this application, only six hazardous disposal landfills remain available for an ever-increasing amount of industrial waste, contaminated soil, and materials removed from locations designated by the EPA as superfund sites. Considering that a new petroleum refinery has not been built in over approximately thirty years, discovery of new major sources of crude oil have been declining over the past decades, and the number of new landfills for waste materials, hazardous and non-hazardous, are not only decreasing, but existing landfills are reaching their capacity, a conversion of waste products into useable byproducts is a requisite to overcome these problems.

Considerable effort and expense has been invested in waste-to-energy and alternate fuels programs, but have fallen short due to technical issues, limited throughput, expensive after-treatment costs, poor operating efficiency, high energy consumption, or non-commercially viable solutions.

This present invention addresses each of the above waste issues and provides an efficient, cost-effective solution to substantially reduce the amount and type of waste transported to the landfills. In addition, the use of microwave energy to overcome the waste disposal problems is simple and elegant, compared to existing methods.

SUMMARY OF THE INVENTION

In accordance with the present invention, in one aspect, there is provided a microwave reduction process to more economically produce high quality syngas and liquid fuels, suitable for direct introduction into an Internal Combustion Gas Turbine (ICGT), in the petrochemical, industrial, and energy markets within a specified and controlled range of Btu content, while operating below current emissions levels set forth by the U.S. Environmental Protection Agency (EPA). Alternately, the output heat from the ICGT may be passed through a heat exchanger in a combined cycle application for the production of electricity, steam, or other waste heat applications. The gas turbine is coupled to an electrical generator to provide electricity for this invention. It is important to note that combustion of only the syngas fuel is sufficient to provide the total electrical requirements for the microwave system and ancillary support equipment, plus excess energy is available for export to the electrical grid. All of the recovered liquid fuel, carbon black, and steel are available as a revenue stream to the customer. For clarity, it should be noted that the heat potential of a scrap tire is approximately 15,500 Btu/lb (36,053 kJ/kg). The recovered syngas contains approximately 18,956 Btu/lb (LHV) (44,092 kJ/kg), the recovered fuel oil contains approximately 18,424 Btu/lb (LHV) (42,854 kJ/kg), and the recovered carbon black contains approximately 14,100 Btu/lb (32,797 kJ/kg). The typical amounts of recovered by-products through microwave excitation of scrap tires, based on a typical scrap tire mass of 20 pounds (9.072 kg) is given in Table 1. It should be noted that operating conditions, such as applied microwave power, applicator pressure, temperature and residence time will determine the gas:oil ratio derived from the hydrocarbon gases identified in Table 1. Data relevant to gas:oil data is presented in FIG. 8.

TABLE 1

| Typical Scrap Tire Reduction By-Products from Microwave Excitation | | | |
|---|---|---|---|
| Hydrocarbon Gases: | 11.8992 lbs. | (5.397 kg) | 59.4958% |
| Sulfur as $H_2S$: | 0.0373 lbs. | (0.017 kg) | 0.1865% |
| Chlorine as HCl: | 0.0014 lbs. | (0.001 kg) | 0.0070% |
| Bromine as HBr: | 0.0125 lbs. | 0.006 kg) | 0.0627% |
| Unspecified: Carbon Black: | 4.8712 lbs. | (2.209 kg) | 24.3560% |
| Metal Oxides/Fillers: | 0.8683 lbs. | (0.394 kg) | 4.3415% |
| Plated High-Carbon Steel: | 2.3101 lbs. | (1.048 kg) | 11.5505% |
| Total: | 20.0000 lbs. | (9.072 kg) | 100.0000% |

When the heat content of the various recovered by-products is considered in conjunction with the mass percentages given in Table 1, an energy balance exists between the heat contained within the scrap tire feedstock and the heat recovered from the microwave-reduced scrap tire by-products. A mass balance is also achieved between the tire feedstock and various recovered by-products.

High power density microwave energy has been utilized effectively to reduce polymers through molecular excitation of polar and non-polar molecules, while producing intermolecular heating within low-loss dielectric materials.

This invention pertains primarily to an improved, non-pyrolytic method and apparatus for: (1) coupling of the microwave energy to the applicator; (2) matching the applied microwave energy from the microwave generator(s) to the volume of material within the applicator(s); (3) diffusion of high power density microwave energy throughout the applicator by the employment of a diffuser matrix employing a plurality of channels; (4) transfer of energy volumetrically to applicator material through improved microwave absorption and thermally conductive techniques; and (5) reduced energy consumption.

The improvements described in this invention result in improved microwave absorption within the material in the applicator, resulting in an even temperature distribution throughout the applicator(s), leading to the more rapid molecular breakdown of organic compounds, such as scrap tires, all types of scrap or discarded mixed plastics, discarded asphalt roofing shingles, and those organic compounds present in Automotive Shredder Residue (ASR), to syngas, fuel oil, and carbon.

This invention also rapidly and safely breaks down hazardous organic materials, such as polychlorinated biphenyls, polycyclic aromatic hydrocarbons, and hexachorobenzene compounds, present as contaminants in soils other materials, to harmless byproducts.

The invention can also using starting materials such as other waste materials including municipal solid waste, construction waste, and computer waste, and significantly reduce their volume and/or directly converted to fuels. Hazardous medical waste is also a feedstock with the concomitant benefit of the total destruction of pathogens contained therein.

The invention additionally encompasses recovery of gas and liquid fuels from hazardous residual material remaining in the bottom of crude oil tankers, residue accumulated at the bottom of crude oil storage tanks, and refinery "bottoms" remaining from processing crude oil, with the remaining hydrocarbon-free solids disposed of in ordinary landfills.

These and other objects of this invention will be evident when viewed in light of the drawings, detailed description and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

The best mode for carrying out the invention will now be described for the purposes of illustrating the best mode known to the applicant at the time of the filing of this patent application. The examples and figures are illustrative only and not meant to limit the invention, which is measured by the scope and spirit of the claims.

The scrap tire material received from the scrap tire processing plant is typically shredded in randomly sized pieces from ½ inch (12.7 mm)×½ inch (12.7 mm) to about 1 inch (25×4 mm)×1 inch (25.4 mm), usually containing all of the steel associated with the scrap tires. Some scrap tire shredders will remove about 60% of the steel, as part of the scrap tire processing for crumb rubber applications. This invention can process shredded scrap tire material with or without the steel Laboratory data indicates that the overall microwave process efficiency increases approximately 10-12% with the reduced steel content in the scrap tire material, due to reduced reflected power, which is more than enough to offset the cost of steel removal during the scrap tire shredding operation.

Figure 1:
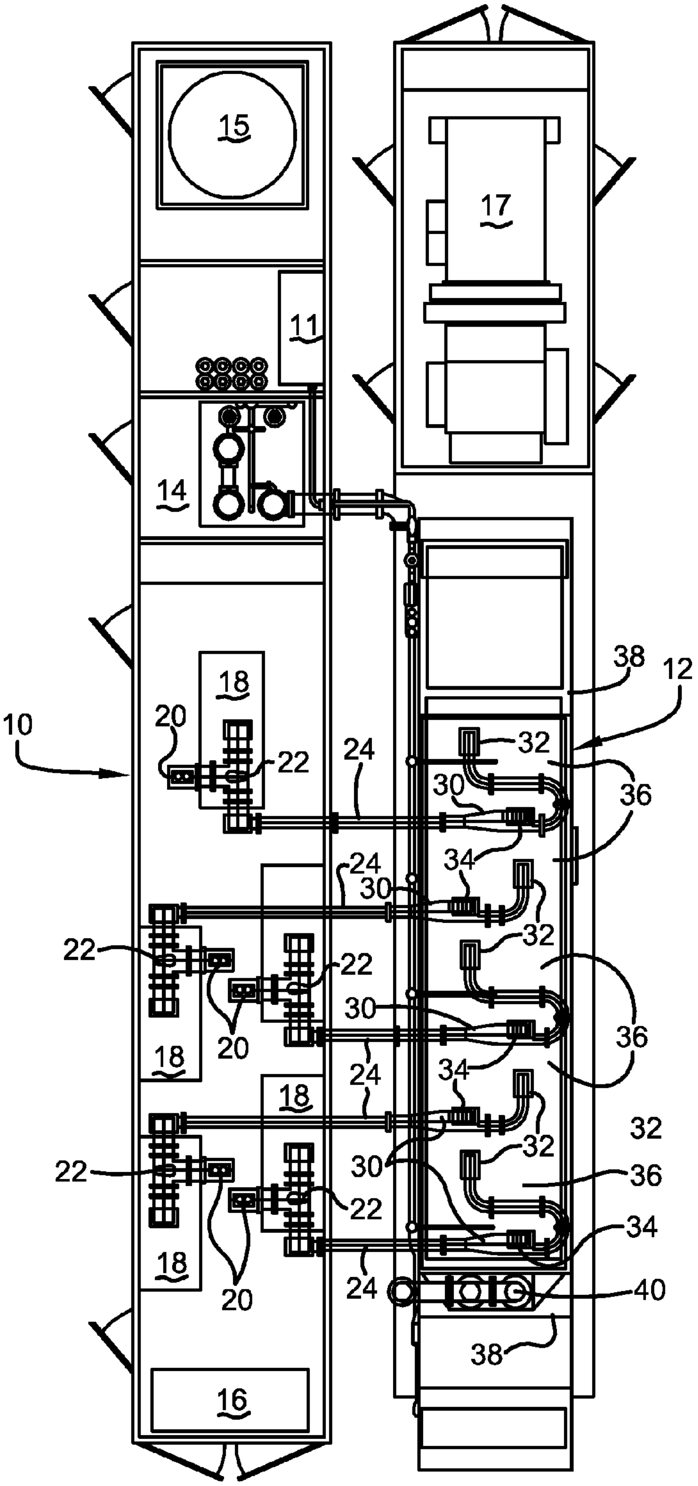
FIG. 1 PRIOR ART
FIG. 1 is a top plan view of a prior art microwave-based reduction system assembly drawing illustrating microwave generators, applicator, chiller, scrubber and nitrogen generator set upon mobile trailers.

As illustrated in FIG. 1, the prior art apparatus includes five (5) major elements (1) a mobile sealed microwave reduction multi-mode applicator 12, coupled to a mobile set of microwave generators 10, (2) a nitrogen generator 11, which displaces any air within the microwave applicator and provides a non-flammable blanketing gas over the organic material under reduction, in this case, scrap tire material, (3) gas process condenser 13, which receives the hydrocarbon vapor stream from the output of microwave applicator, (4) a gas-contact, liquid scrubber 14, which removes 99.99% of the hydrogen sulfide, hydrogen chloride, and hydrogen bromide contaminants, (5) a air-water chiller 15, which provides continuous cooling water to the magnetrons and control cabinets for heat rejection, and (6) an electrical generator 17, sized to provide all electrical energy to the microwave system and ancillary equipment.

Within the prior art mobile set of microwave generators 10, are illustrated five (5) individual microwave generators 18 in continuous electronic communication and controlled by a PLC in main control panel 16. Each microwave generator has a magnetron 20 and a microwave circulator 22 with water load. The generated microwaves are coupled from each microwave generator 18 to microwave reduction applicator 12 via rectangular waveguides 24. In the particular microwave reduction system shown in FIG. 1, an exhaust fan 40 is illustrated with associated motor 42 to extract the hydrocarbon vapor from applicator 12 and convey the vapor stream to process gas condenser 13.

Figure 4:
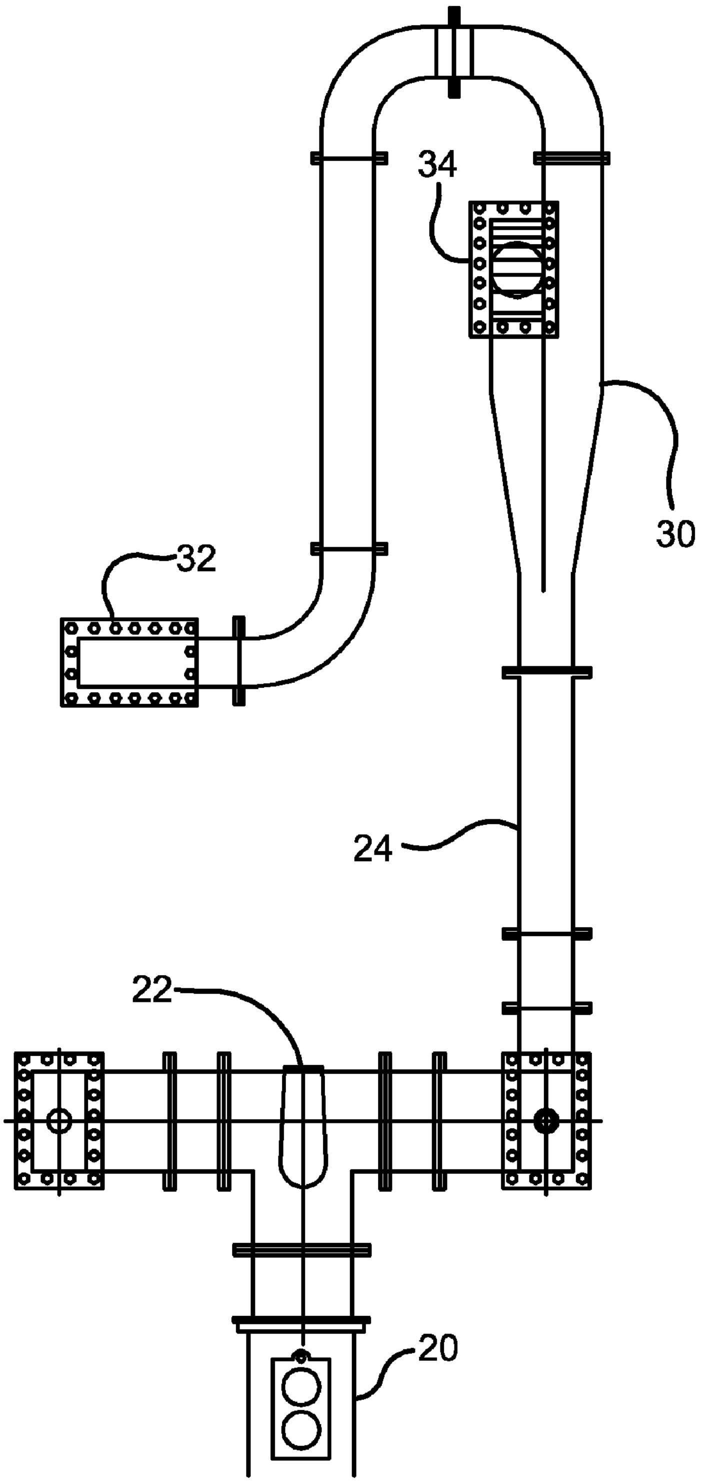
FIG. 4 PRIOR ART
FIG. 4 is an enlarged top view of a prior art bifurcated waveguide assembly.
Figure 5:
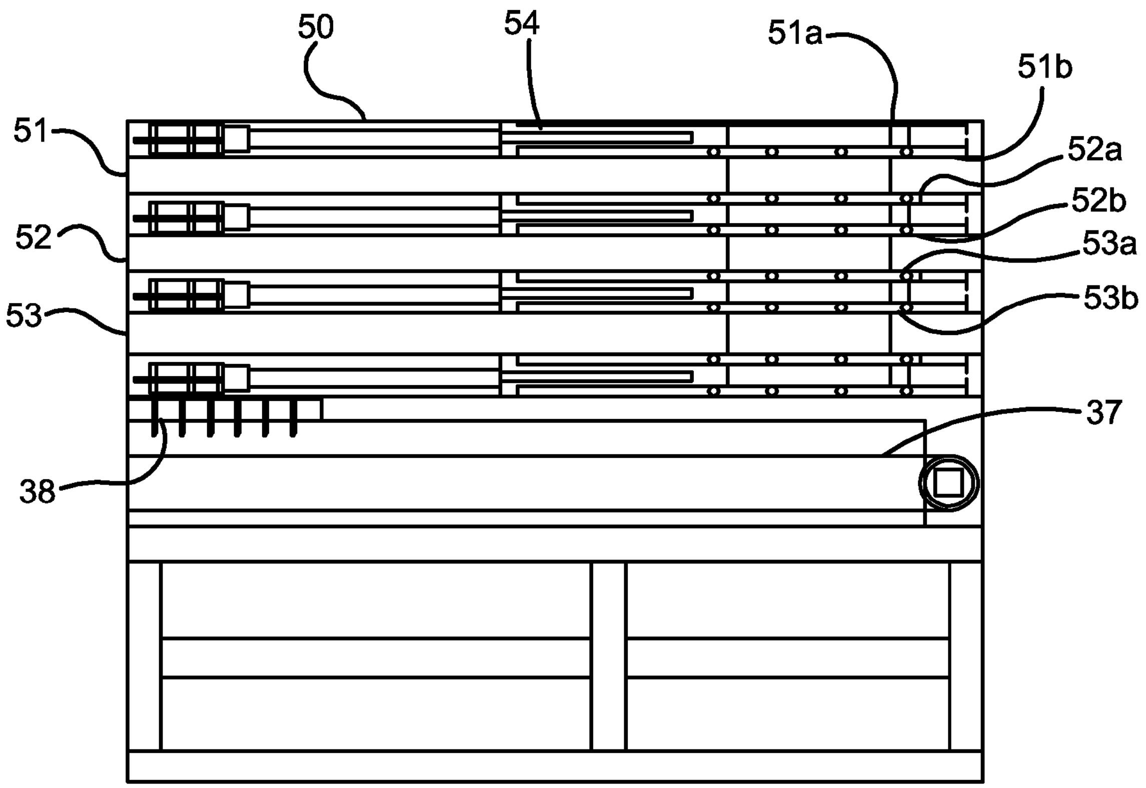
FIG. 5 PRIOR ART
FIG. 5 is a side plan (elevation) view of the prior art infeed assembly.
Figure 6:
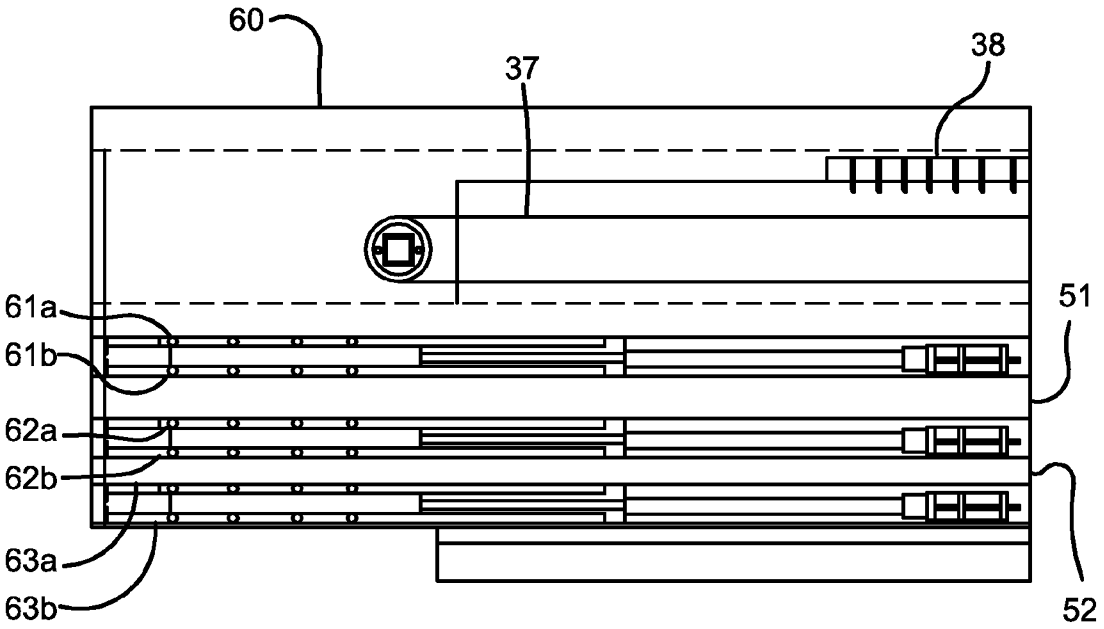
FIG. 6 PRIOR ART
FIG. 6 is a side plan (elevation view) of the prior art outfeed assembly.

In its original design, each waveguide assembly 31, which is illustrated in FIG. 4, contains a bifurcated waveguide assembly 30, which directs the microwave energy into specific microwave entry ports 36 in a direction collinear 32 with the longitudinal plane of the applicator conveyor belt 19 and normal 34 to this same longitudinal plane. Microwave leakage outside of the sealed applicator is eliminated by an RF trap 38, consisting of an array of choke pins, designed to a length appropriate for the operating frequency. This original design is now supplanted by the design illustrated in FIGS. 11-14, discussed herein.

Figure 2:
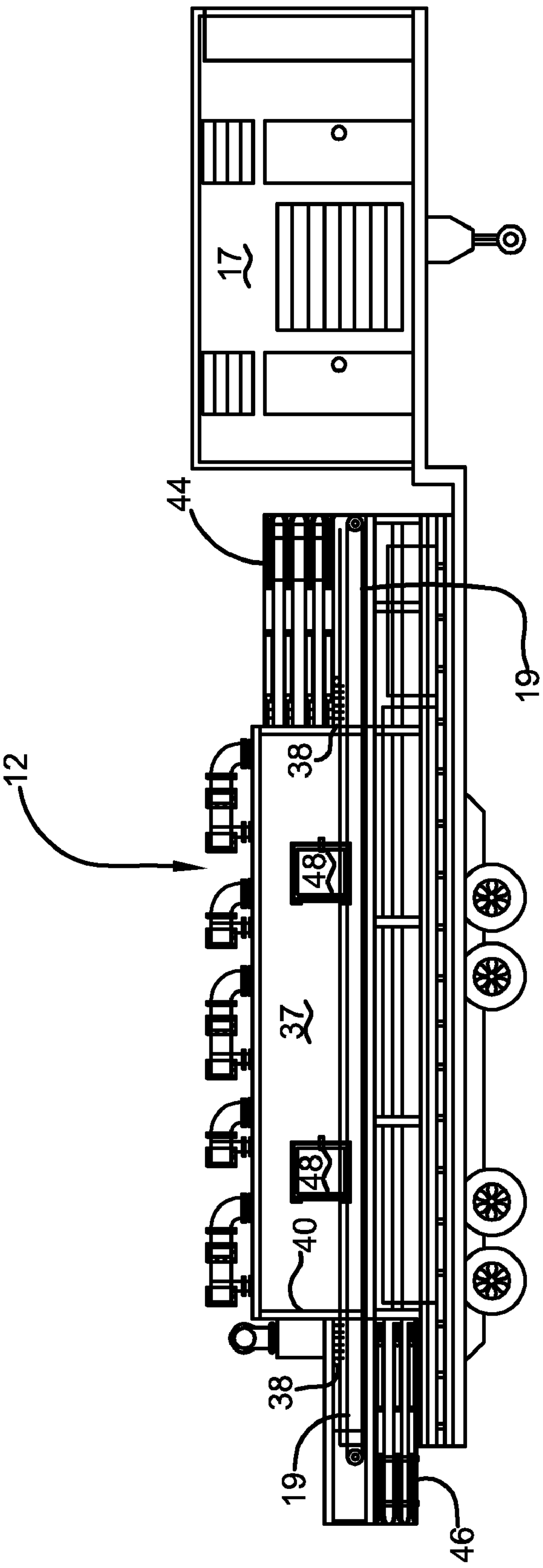
FIG. 2 PRIOR ART
FIG. 2 is a side plan (elevation) view of the prior art microwave applicator trailer showing an infeed assembly, tractor-fed belt, cooling water tanks, diesel fuel day tank, and outfeed assembly.

As illustrated in FIG. 2, prior art microwave reduction applicator 12 has one entry port 44 and one exit port 46, which are in longitudinal communication with a closed-mesh, continuous, stainless steel belt 19, said belt being of mesh composition, set within a pair of side guides, and having longitudinal raised sides for retention of the sample, said sides being approximately 4 inches (10.16 cm) in elevation. As illustrated, there are two access-viewing ports 48 positioned on each side of microwave reduction applicator 12. Illustrated in FIG. 1 and FIG. 2 are multiple microwave reduction applicators 12, which are interconnected to form a continuous chamber 37. Each prior art microwave reduction applicator 12 consisted of two (2) or four (4) waveguide 36 entry ports, depending on the specific application and the microwave power required for the application. While a total of three (3) applicators 12 were shown, both larger and smaller numbers of applicators 12 necessary to arrive at an application-specific chamber 37 length, were envisioned to be within the scope of the invention. In fact, the invention worked with only one (1) applicator chamber 37, with only two (2) entry ports.

In the prior art arrangement, the microwave energy was coupled from microwave generator 10 to the applicator via rectangular waveguide assembly 31 and exited the same through bifurcated waveguide assembly 30. The source of the microwave energy is a magnetron, which operates at frequencies, which range from 894 MHz to 2450 MHz, more preferably from 894 MHz to 1000 MHz, and most preferably at 915 MHz+/−10 MHz. The lower frequencies are preferred over the more common frequency of 2,450 MHz typically used in conventional microwave ovens due to increased individual magnetron power and penetration depth into the organic material, along with an increase in operating efficiency from 60% in the case of 2450 MHz magnetrons, to 92% for 915 MHz magnetrons. Each magnetron has a separate microwave generator control panel in electronic communication with a main control panel for system control.

Figure 3:
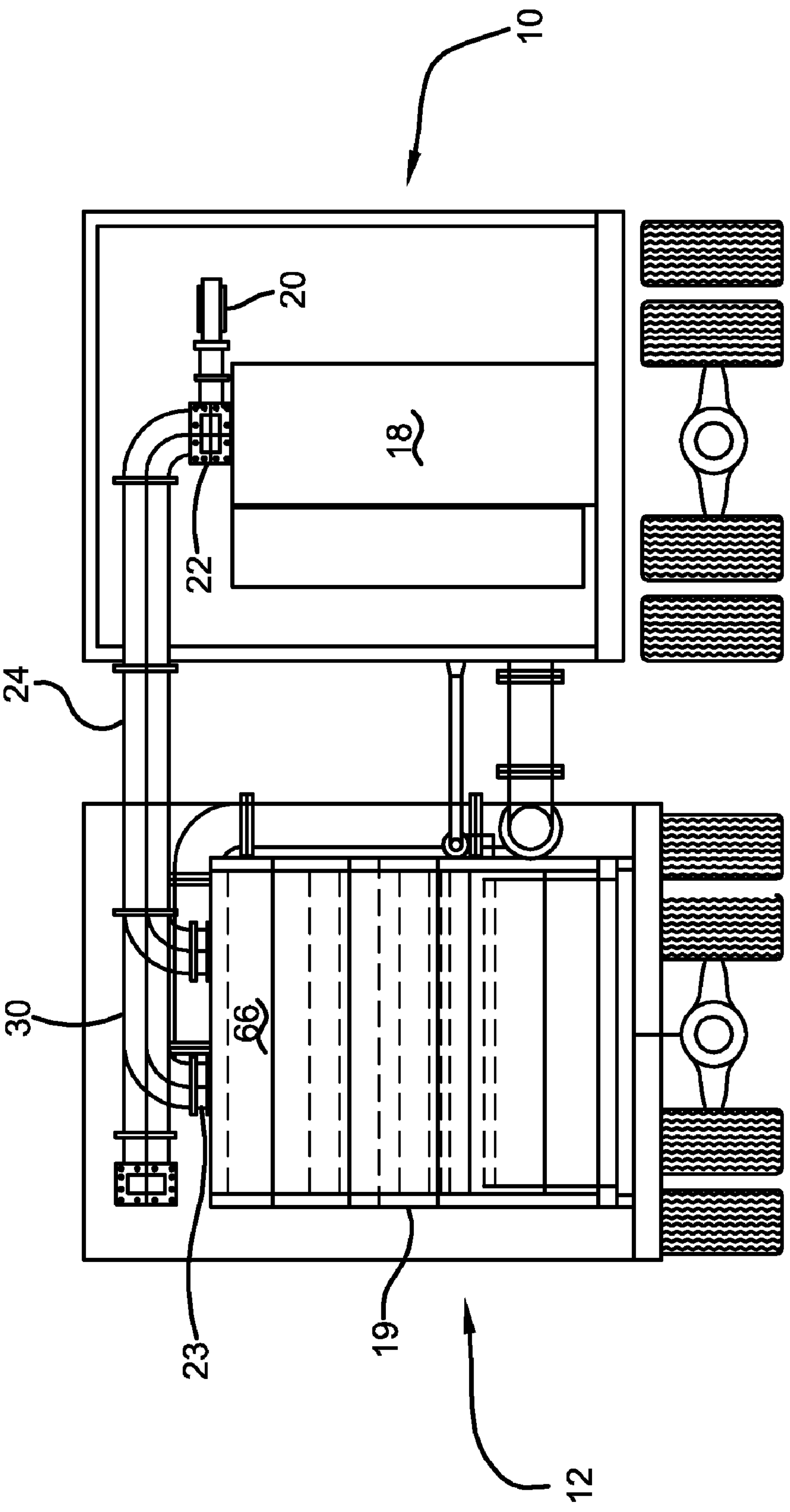
FIG. 3 PRIOR ART
FIG. 3 is a rear plan view of the prior art assembly of FIG. 1.

As shown in FIG. 3, the microwave reduction applicator has an active area, whose boundaries are set by interior roof sheets 21 and stainless steel belt 19. For the applicator described in this invention, the active microwave reduction chamber height is 24 inches (60.96 cm). It is well known how to appropriately size the active area of microwave chamber 37. Belt 19 traverses through the active area between two (2) continuous guides 21, whose open dimension is sufficient for belt 19 to pass, but is not a multiple or sub-multiple of the microwave frequency. The height of guides 21 is a nominal 4" (10.16 cm), which will contain the material on belt 19. The closed-grid belt provides the lower reference, which becomes the bottom of the active area of the applicator.

In the event that the microwave energy is not absorbed by the organic material, a condition, which results in reflected microwave energy, this energy is redirected by a device known as a circulator 20 and subsequently absorbed by a water load 22. The circulator is sized to absorb 100% of the microwave energy generated by the magnetron. Each magnetron transmits its energy via waveguide 24 through quartz pressure window assembly 23, into the series-connected microwave reduction chamber(s). Quartz pressure window assembly 23 includes two flanges separated with rectangular waveguide, one (1) wavelength long, each flange containing a milled recess to accept a ¼" thick fused quartz window, which is microwave-transparent. This quartz pressure window assembly 23 is installed between waveguide 24 and either microwave entry port 32 or 34 into applicator chamber 37 to contain the pressure within the microwave reduction chamber and prevent any potentially hazardous gas from entering the waveguide system back to microwave generator 10. Quartz pressure windows assembly 23 is pressurized with nitrogen from nitrogen generator 11, and referenced to the internal microwave reduction chamber pressure. This insures that excess pressure cannot build up on the reduction chamber side of the quartz window assembly, resulting in a failure of the quartz window, and, with the introduction of air into the reduction chamber, create a fire or explosion hazard. In a preferred embodiment, each microwave generator operates at a center frequency of 915 MHz+/−10 MHz. In an expanded view in FIG. 4 this microwave energy is coupled from the microwave generator, through a bifurcated waveguide assembly, into applicator chamber 37 via two (2) waveguides 32,34, which serve as rectangular conduits into each applicator chamber 37. The improvement to this prior art arrangement for the dual pressure windows is illustrated and discussed in pertinent part with reference to FIGS. 13-14.

In the original configuration, the waveguide entry into this applicator is via a three-ported bifurcated waveguide assembly 30, which equally divides the electromagnetic wave of microwave energy prior to the two-plane entry into the top of the applicator chamber, while maintaining electric field dominance. The waveguide 32,34 inputs to the applicator chamber 37 from the bifurcated waveguide assembly 30 are in the same plane on the top of the applicator 37, but one waveguide plane 32 is oriented along the x-axis, while the other waveguide plane 34 is oriented along the y-axis. The split waveguide assemblies illustrated in FIG. 4 are designed so as to produce microwaves, which are essentially 90° out of phase. This results in the generation of multiple modes of microwave energy within applicator chamber 37 and elimination of the requirement for mode stirrers, while providing a more uniform distribution of the microwave energy throughout applicator 12.

The microwave energy is produced by the microwave generator and transmitted into a WR-975 standard rectangular waveguide, fabricated from high-conductivity, low-loss 1100S aluminum, instead of the more conventional 6061 aluminum. The choice of low-loss aluminum results in less losses throughout the waveguide system from the microwave generator output to the microwave reduction chamber inputs. It is recognized however, that low-loss aluminum 3003-H14 and similar compositions are applicable to this invention in its current form.

Generally, when mobile units are desired, with the microwave generators mounted on one trailer and the applicator mounted an adjacent trailer, it is customary to accomplish coupling of the microwave energy between the two trailers via a ribbed, flexible waveguide assembly. However, there is also a tendency for those performing field alignment of the two trailers to bend the flexible waveguide beyond its specified limits of +/−0.010 inches (0.254 mm), resulting eventually in a crack or fatigue failure of the flexible waveguide assembly. Failure of any joint in the waveguide assembly will cause microwave leakage into the surrounding area, resulting in a hazard to personnel and potentially interfering with communications equipment. It is understood that flexible waveguides may be used for this application, but are not shown in the drawings. It is also within the scope of this invention to have the microwave unit positioned on floating base frame assembly 82, as better illustrated in FIG. 11 which illustrates a more compressed footprint design.

In the original configuration, the microwave energy exits the microwave generator trailer and enters a bifurcated waveguide assembly 30, which is illustrated in FIG. 4. One output connects to a right angle waveguide section, from which the microwave energy enters directly into microwave chamber 37. The other output is presented to a two-section, long-radius, right angle waveguide section, which accomplishes the turning of the microwave energy path 180°, while maintaining electric field dominance. The microwave energy enters a short straight section and another long-radius, right angle waveguide section. The microwave energy is then coupled into a right angle waveguide section and enters through quartz pressure window assembly 23 directly into microwave reduction chamber 37.

In the original arrangement, although waveguide entries 32,34 into applicator reduction chamber 37 are in the same plane on the top of applicator 12, the orientation of the two waveguide entries 32 and 34 relative to the centerline of the applicator, is 90° to each other. One waveguide entry section to each applicator entry point is parallel to the flow of the organic materials, while the other is perpendicular to the flow of the organic material. The other significant feature of this design is that the distance from the output from the bifurcated waveguide, which couples the microwave energy to the applicator entry point parallel to the flow of the organic material, is physically much longer than the output feeding the perpendicular port. This additional length results in a different characteristic impedance at the microwave chamber entry point, a time delay in the microwave energy reaching the applicator entry point, and a relative phase shift in the energy wave itself. As stated previously, the microwave generator operates at a center frequency of 915 MHz+/−10 MHz. At this frequency, the effects of additional waveguide lengths and bends present a very noticeable change in the time/phase relationships due to the impedance mismatch. The impedance mismatch results in a phase shift of 90 electrical degrees. The significance of the 90° phase shift manifests itself in the type of polarization present in the microwave reduction chamber. Each microwave input from the bifurcated waveguide assembly is a linear polarized wave. When two linear polarized waves, separated in time quadrature by 90°, circular polarization occurs. In this invention, the impedance mismatch, phase shift in microwave inputs to the applicator, and resulting circular polarization, along with the chosen frequency of operation, is a significant contribution to the microwave energy mixing within each microwave reduction chamber, allowing more even microwave energy distribution throughout the entire applicator.

Microwave reduction occurs in a continuous mode, as opposed to a batch mode, and organic material is continuously, but synchronously, entering and exiting the microwave applicator. During the entry and exit times, it could be possible that microwave energy could propagate into the surrounding area, resulting in a possible hazard to personnel and create radio frequency (RF) interference. To prevent leakage of microwave energy from the active area of the microwave applicator, a device known as an RF trap 38, containing a matrix or array of grounded ¼-wavelength RF stubs (antennae), with ¼-wavelength spacing between the RF stubs in both the x-plane and y-plane, are installed at each end of the applicator to insure attenuation of microwave energy for compliance with leakage specifications of <10 $mW/cm^2$ maximum for industrial applications and <5 $mW/cm^2$ maximum for food applications.

As described with particular reference to an original configuration, the active area in the microwave chamber consists of a rectangular cavity, measuring 8 feet long (2.44 meters)×4 feet (1.22 meters) wide×2 feet (0.61 meters) high, designed specifically for the microwave energy coupled from one (1) or two (2) microwave generators. This is referred to as a microwave reduction chamber or one applicator module. Multiple microwave reduction chamber modules may be connected together to form an applicator. FIG. 1 illustrates a microwave reduction applicator which includes three (3) microwave reduction chambers, which receive microwave energy from five (5) microwave generators and five bifurcated waveguide assemblies, which result in ten (10) sources of microwave energy to the applicator and even more uniform microwave energy distribution. The applicator also contains a continuous, self-aligning, closed mesh, 4 feet (1.22 meters) wide, Type 304 stainless steel belt 19, which transports the organic material into the applicator at entry port 44, through the active area of applicator 45, and out of exit port 46.

Just as applicator 12 and microwave 10 are chosen to accommodate a specific throughput of scrap tire material equivalent to 100-8,000 tires per day, infeed 50 and outfeed 60 assemblies, along with microwave reduction chamber 37 are also sized volumetrically to process the specified amount of material. As this invention is capable of operating in continuous mode, as opposed to batch mode, the feed systems operate independently, yet synchronously with the movement of the material on belt 19 though applicator reduction chamber 37.

Initially, applicator reduction chamber 37 is purged with five (5) volumes of nitrogen gas to displace any air within, and is maintained in a slightly pressurized state, approximately 0.1 psig (0.689 kPa) above local atmospheric pressure. This insures that no air migrates into applicator reduction chamber 37 during opening of either infeed 50 or outfeed 60 shutter systems. Since the applicator is slightly pressurized, nitrogen will flow toward the sealed shutter assemblies, instead of air flowing into the microwave reduction chamber. With reference to FIG. 3 and FIG. 4, the microwave reduction chamber is open to the bottom slide 53*b* of shutter 53 and the top slide 61*a* of shutter 61. If any seal leakage occurs at the shutter interface, the nitrogen direction of flow is always from the applicator into the shutter assembly. At startup, all slides on infeed shutter system 50 and outfeed shutter system 60 are closed.

Infeed system 50 includes three sliding shutter assemblies, 51, 52, and 53. The sequence of operation is as follows: Initially, nitrogen gas is applied to infeed shutters 51, 52, and 53 until five (5) volumes have been purged through the shutters to atmosphere. The top slide 51*a* of shutter 51 opens and receives material from an optional hopper or external conveyor belt. The bottom slide 51*b* of shutter 51 remains closed. Dependent upon desired throughput, load cell 54 under the top slide allows material to enter shutter 51 until the prescribed amount of material has been deposited. At this time, top slide 51*a* closes and nitrogen purge gas is applied to shutter 51. After five (5) volumes of nitrogen have purged shutter 51, bottom slide 51*b* opens, along with slide 52*a* of shutter 52, located directly below shutter 51. After the material drops through from shutter 51 into shutter 52, bottom slide 51*b* and top slide 52*a* close. After five (5) volumes of nitrogen have purged shutter 52, bottom slide 52*a* opens, along with slide 53*a* of shutter 53, located directly below shutter 52. After the material drops through from shutter 52 into shutter 53, bottom slide 52*b* and top slide 53*a* close. After five (5) volumes of nitrogen have purged shutter 53, bottom slide 53*b* opens, and the material drops onto conveyor belt 37. Conveyor belt 37 transports the material beneath RF trap's 38 array of choke pins into the active area of the microwave reduction chamber. Based upon the type of material, throughput required, and microwave power applied, conveyor belt 37 transports the material through applicator 12 at a preset speed.

Outfeed system 60 includes two sliding shutter assemblies, 61 and 62. The sequence of operation is as follows. Initially, nitrogen gas is applied to outfeed shutters 61 and 62 until five (5) volumes have been purged through the shutters to atmosphere. When belt 37, along with its reduced material reaches the outfeed shutter system, nitrogen purge gas is applied to outfeed shutter 61 to displace any air. Top slide 61*a* of shutter 61 opens and the reduced material drops from conveyor belt 37 into outfeed shutter 61. Bottom slide of shutter 61*b* remains closed. After the material drops from the belt into shutter 61, top slide 61*a* closes. Nitrogen purge gas is applied to shutter 62 until five (5) volumes have been purged through shutter 62 to displace any air. Then, bottom slide 61*b* of shutter 61 and top slide 62*a* of shutter 62 open, and the material falls into shutter 62, located directly below shutter 61. When all of the material has dropped into shutter 62, bottom slide 61*b* of shutter 61 and top slide 62*a* of shutter 62 closes. Nitrogen gas is applied to shutter 63 until five (5) volumes have been purged through shutter 63. Then bottom slide 62*b* of shutter and top slide 63*a* of shutter 63 open, and the material falls into shutter 63, located directly below shutter 62. Finally, bottom slide 63*b* of shutter 63 opens and the reduced material drops into an optional grinder, onto an external conveyor belt, into an optional hopper, or is removed by a vacuum system to a storage area. Sequencing of the infeed system, conveyor belt speed control, outfeed system, magnetrons and nitrogen purge gas system is under PLC program control at all times. An alternate infeed and outfeed system includes a nitrogen-purged, multiple-chamber rotary airlock system.

The internal walls of the applicator are made from either low-loss 1100S aluminum plate or Type 304 stainless steel, depending upon the application. High temperature applications in excess of 900° F. (482° C.) and corrosive atmospheres require the use of Type 304 stainless steel. Microwave reduction of scrap tires results in an equilibrium temperature occurring at 680° F. (360° C.) in a relatively non-corrosive atmosphere, therefore, 1100S aluminum plate is the material of choice. In microwave reduction applications such as plastics, particularly polyvinyl chlorides (PVC), hydrochloric acid is produced in voluminous amounts, contributing to surface corrosion, as well as stress corrosion cracking; therefore, Type 304 stainless steel is preferred The type of gaskets used around microwave viewing/access doors 48 for gas containment requires a round silicone gasket for non-corrosive atmospheres or a Teflon-enclosed epoxy gasket for corrosive atmospheres. In either application, a carbon-filled Type 304 stainless steel mesh gasket is used for microwave containment around viewing/access doors 48. The hydrocarbon gases exit through a transition plenum duct from a rectangular cross-section at the applicator to a circular cross-section to accommodate a ten (10) inch (25.4 cm) pipe containing a tee, whose branch is connected to a rupture disk 44 rated at 15 psig (103.4 kPa), and a rotary-disk butterfly valve 41. Applicator discharge valve 41 serves to control the applicator static pressure, which is the result of the hydrocarbon gases generated during microwave reduction of the organic materials plus nitrogen purge gas.

The five (5) microwave generators, as shown in FIG. 1, consist of five (5) magnetrons, each rated at 100 kW, five (5) circulators with water loads, each rated at 100% power generated by their respective magnetrons, and five (5) switched-mode power supplies (SMPS), which contain all power and control signals, along with metering for the magnetrons and control electromagnets, plus digital and analog interfaces to the Programmable Logic Controller (PLC). The SMPS operates at a typical efficiency of 91%, and eliminates the less efficient, heat-producing power transformer, along with the six-phase bridge rectifier assembly, SCR controllers, filtering, and associated wiring. The additional benefit of the SMPS is that, in the event of an immediate shutdown, the output voltage of the SMPS almost immediately (<10 mS) decreases to zero (0) volts. However, in the case of the transformer power supply, the internal capacitance between the transformer windings, can store a lethal voltage for several hours. The other undesirable effect from the transformer power supply is that after a shutdown, the stored charge within the transformer can cause the magnetron to operate outside its rated operating envelope and cause premature magnetron failure.

The PLC provides metering, sequencing and control of the microwave generator, conveyor motors and applicator controls. The only additional requirement is cooling water in the amount of 5 gallons per minute (18.93 liters/minute) per 100 kW magnetron and 3 gallons per minute (11.35 liters per minute) per circulator water load. Each microwave generator is a two-door enclosure with front and rear door access, measuring 48 inches (1.22 meters) long×84 inches (2.13 meters) high×24 inches (0.61 meters) deep, which is a footprint reduction from conventional microwave generator systems.

To process additional material or increase the throughput, one may add additional microwave generators, microwave applicator modules, increase belt speed, or increase the organic material bed depth proportionally. For small variations in the power requirement due to slight inconsistencies in the material being processed, the belt speed may be adjusted to change the dwell or residence time of the organic material within the applicator. Belt speed control is accomplished by changing the conveyor speed setpoint on the touchscreen, mounted on the front of the Main Control Panel, adjacent to the line of microwave generator panels, as illustrated in FIG. 1.

It has been determined that the process characteristics relative to throughput and power consumption are linear from minimum to maximum throughput. For example, energy consumption during microwave reduction of scrap tires at 915 MHz is 1.80 kW-hr per tire from 100 tires per 8-hour shift to 8,000 tires per 24-hour day, when utilized with an appropriate applicator length, bed depth and microwave power level. This invention allows the addition of microwave generators and relative appurtenances in sets of six, along with an extension of the applicator as dimensionally defined above.

The standard design, which supports the majority of organic material reduction processes with high power density microwaves, contains three (3) microwave modules per applicator. Through careful design, this modular concept may be extended to include a maximum of 80 microwave generators or 16 modules within one applicator, in a stationary design.

In one aspect of the invention, the design of the unit is a mobile demonstration unit, with the microwave generators and control cabinets, along with the Main Control Panel, scrubber, nitrogen generator and chiller mounted in one trailer and the microwave applicator assembly and electrical generator mounted on an adjacent trailer.

Microwave system control is accomplished by the use of a Programmable Logic Controller (PLC) with Digital and Analog Input/Output (I/O) Modules and a Data Highway to a Remote Terminal Unit (RTU), which are all mounted in the Main Control Panel (MCP). The RTU is also known as an Operator Interface Terminal (OIT), as the touchscreen on the OIT is the operating interface to the microwave reduction system. PLC communications modules are mounted in each microwave generator enclosure, which permits continuous bidirectional communication between the PLC and the OIT or touchscreen. The PLC program provides continuous sequencing, monitoring and control functions in real time. The PLC program also communicates along a data highway to display alarm/shutdown status and operating parameters on the touchscreen The touchscreen provides multiple displays in both digital and analog formats in real time. The summary status touchscreen indicates power output, reflected power, anode current, anode voltage, filament current, electromagnet current, generator cabinet temperatures, applicator temperatures and pressures, internal and external water temperatures, hydrocarbon vapor flow rates, process operating curves, PID control loop status, and parametric data from the nitrogen generator, chiller, process condenser, and scrubber, all in real time.

Additional magnetron protection is insured by a directional coupler system, which monitors forward and reflected power, and de-energizes the high voltage to the magnetron in the event of sensing more than 10% reflected power. An arc detection system further protects the magnetron, three-port circulator, and waveguide by de-energizing the high voltage upon detection of arcing within the applicator. Fire detection within the applicator includes infra-red (IR) sensors, smoke detection and rate-of-rise temperature detectors plus combustible gas detectors adjacent to the applicator, which are all wired in series with the safety shutdown system. A multiple-bottle nitrogen backup system serves as a deluge system in the event of a fire, plus provides nitrogen backup, in the event of a nitrogen generator failure.

Any shutdown parameter, which exceeds its preset limit, initiates an immediate shutdown of the high voltage system, and enables the safety shutdown system to proceed through an orderly and controlled shutdown. The safety shutdown system includes both fail-safe hardwired circuitry and PLC shutdown logic, along with local and remote emergency stop buttons to insure maximum protection for operating and maintenance personnel and equipment. Microwave access/viewing doors, microwave generator doors, and power supply enclosure doors are provided with fail-safe, safety switches, which are interlocked with the PLC program, and monitored during microwave operation to protect operating and maintenance personnel from exposure to microwave energy and shock hazards.

Further, the applicator access/viewing doors contain slotted ¼-wavelength chokes and dual fail-safe safety switches, interlocked with the PLC program to immediately (10 mS) switch off the high voltage, in the event of opening during operation. Switching off the high voltage immediately suspends magnetron operation, and hence eliminates any output of microwave energy. Other safety equipment integrated into this invention include a dual-keyed, fused manual disconnect for the main power source from the electrical generator or the customer's utility and a high speed molded case breaker, with electrical trip and shunt voltage trip tied to the shutdown system. Finally, a copper ground bus bar dimensioned 24 inches (0.61 meters) long×2 inches (5.08 cm) high×¼ inch (6.35 mm) thick is provided to insure absolute ground integrity from the main power source to all equipment included with this invention.

PLC programming utilizes standard ladder logic programming, reflecting hardwired logic for digital inputs and outputs, whose logic functions are programmed with Boolean expressions. Special function blocks, including preset setpoints, are used for analog inputs and outputs. The emergency shutdown switches are normally closed (push to open), the low level switches must reach their setpoint before operations may be sequenced, and the high level switches will open upon exceeding their setpoint. Any open switch in the series shutdown string will cause the master shutdown relay to de-energize, which results in de-energizing the high voltage circuits and forces the PLC to execute an immediate, sequential, controlled shutdown.

The best mode for carrying out the invention will now be described for the purposes of illustrating the best mode known to the applicant at the time of the filing of the application. The examples are illustrative only and not meant to limit the invention, as measured by the scope and spirit of the claims.

A summary of recorded data from microwave excitation of scrap tire material is presented in Table 2. All data were the result of exposing shredded scrap tire material to high-power density microwave energy in an approximately one cubic meter (1 $m^3$), stainless steel applicator, fed by microwave inputs from three (3) magnetrons, each capable of generating 3 kW of microwave power at approximately 50% efficiency and operating in batch mode at 2450 MHz. Variations in the output gas compositions, as well as the amounts of gas and oil, were the result of varying the applicator pressure and hydrocarbon vapor residence time. Variations in the applicator pressure and hydrocarbon vapor residence time were the result of varying the position of the applicator output valve. It was observed that higher applicator pressure (2-10 psig) (13.8–6.9 kPa) and lower flow produced a longer hydrocarbon vapor residence time, which resulted in production of more paraffins, less olefins, less arenes and naphthenes, and subsequently less oil. Conversely, lower applicator pressure (0.1-1.0 psig) (0.69–6.9 kPa) produced a shorter hydrocarbon vapor residence time, which resulted in production of less paraffins, more olefins, more arenes and naphthenes, and subsequently more oil.

Applicator pressure was set statically during the nitrogen purge cycle at the beginning of each test between 0.1 and 0.5 psig (0.69–3.45 kPa). Steady-state temperatures reached at equilibrium, occurred at approximately 680° F. (360° C.), with a hydrocarbon vapor residence time of approximately 285 milliseconds (mS).

To verify the effects of pressure, temperature and residence time on the gaseous and liquid fuels produced, pressure within the applicator was increased to a level between 1.0 and 10.0 psig (6.9-69 Pa) by adjusting the applicator discharge valve position closed between 100 and 50% of stroke, respectively. The corresponding pressure setup changes produced a new steady-state temperature, which stabilized in a range of 842-680° F. (450-360° C.), along with a corresponding change in the hydrocarbon vapor residence time within the applicator in a range of 400-80 milliseconds, respectively. Applicator pressure, temperature, and hydrocarbon residence time varied inversely with the closing stroke (less open) of the applicator discharge valve.

Figure 7:
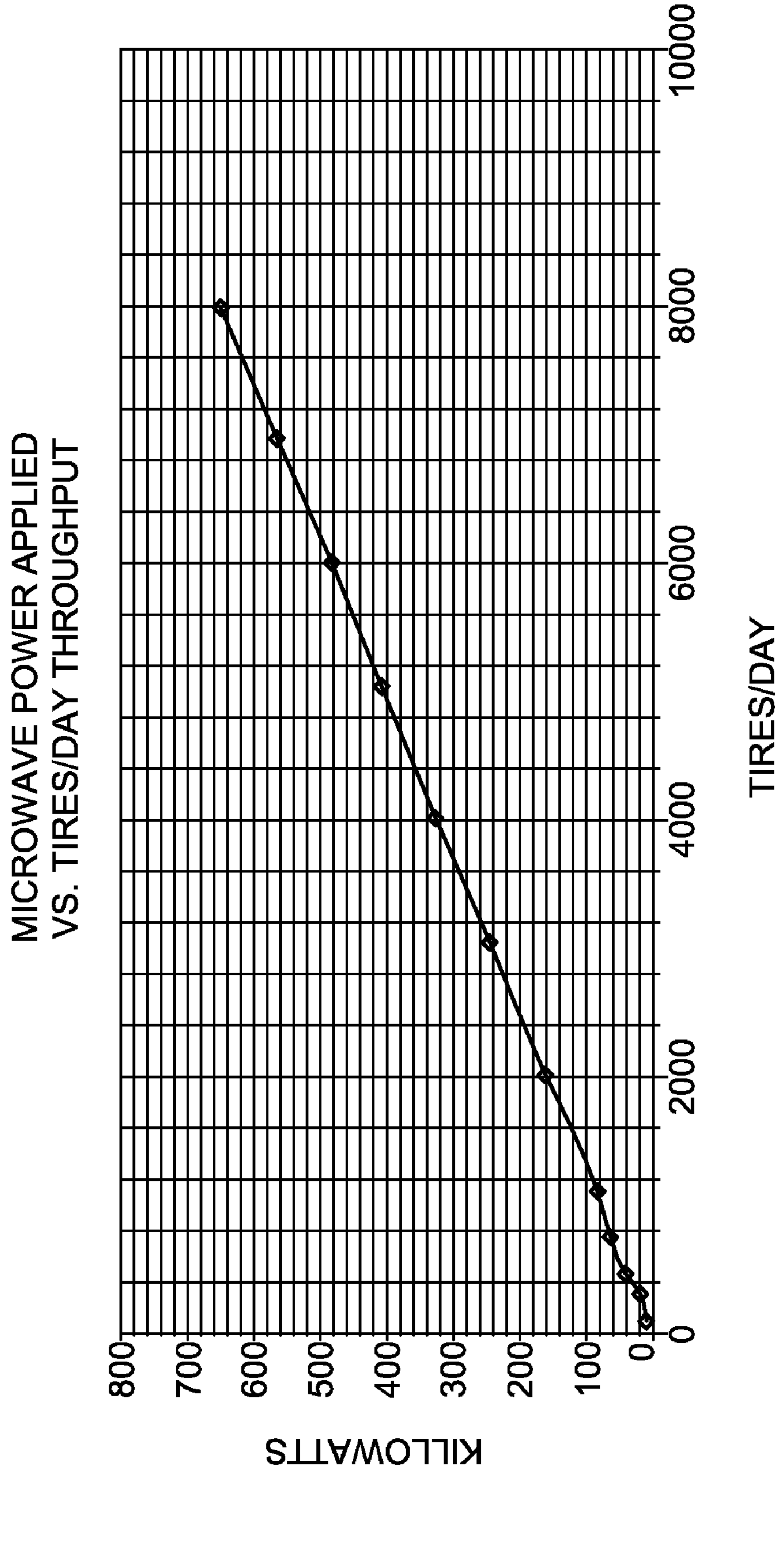
FIG. 7 is a graph illustrating applied microwave power in kilowatts vs. throughput of scrap tires per day of the prior art.
Figure 8:
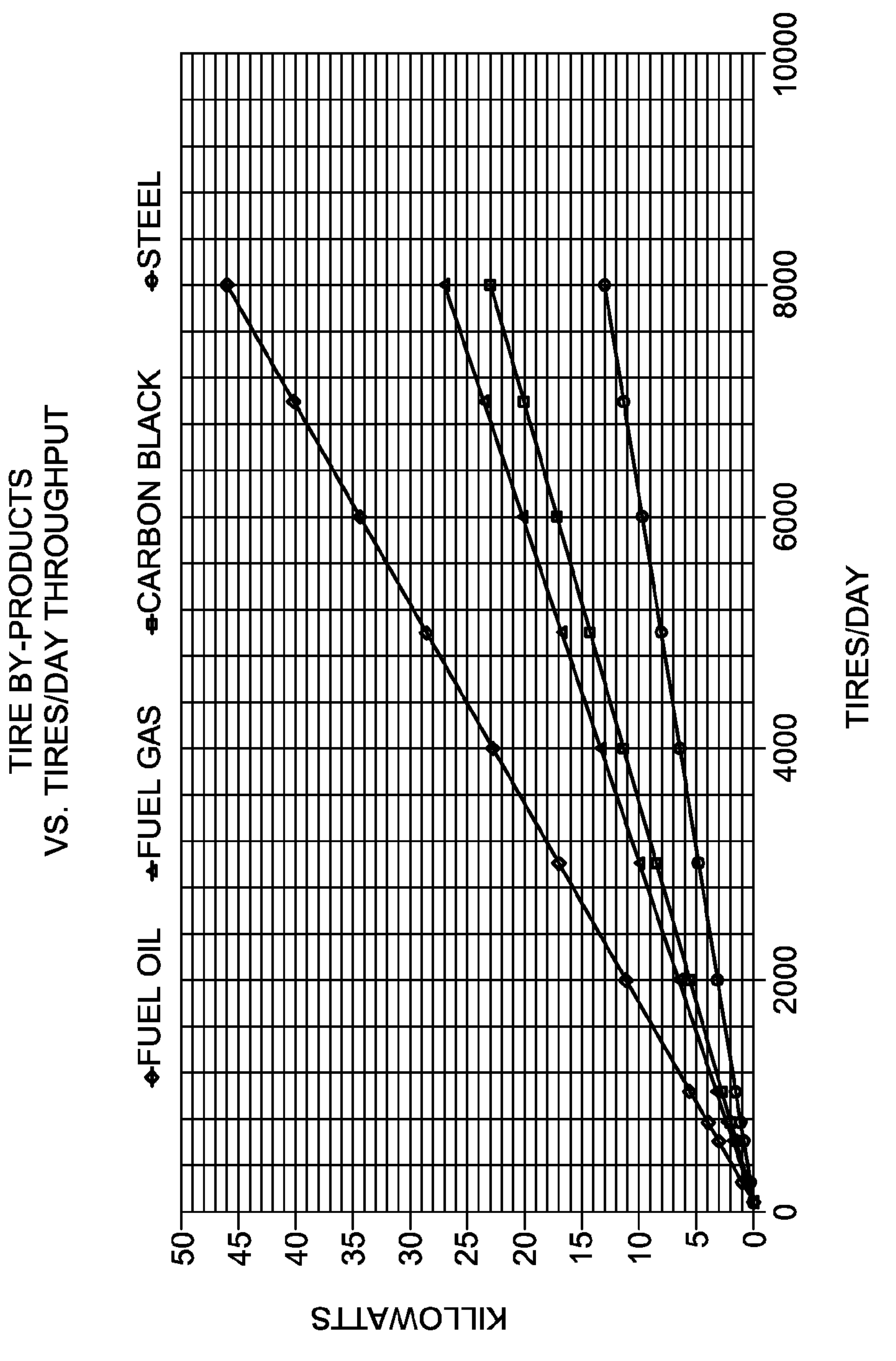
FIG. 8 is a graph illustrating by-products recovered from scrap tires vs. applied microwave power in kilowatts of the prior art.
Figure 9:
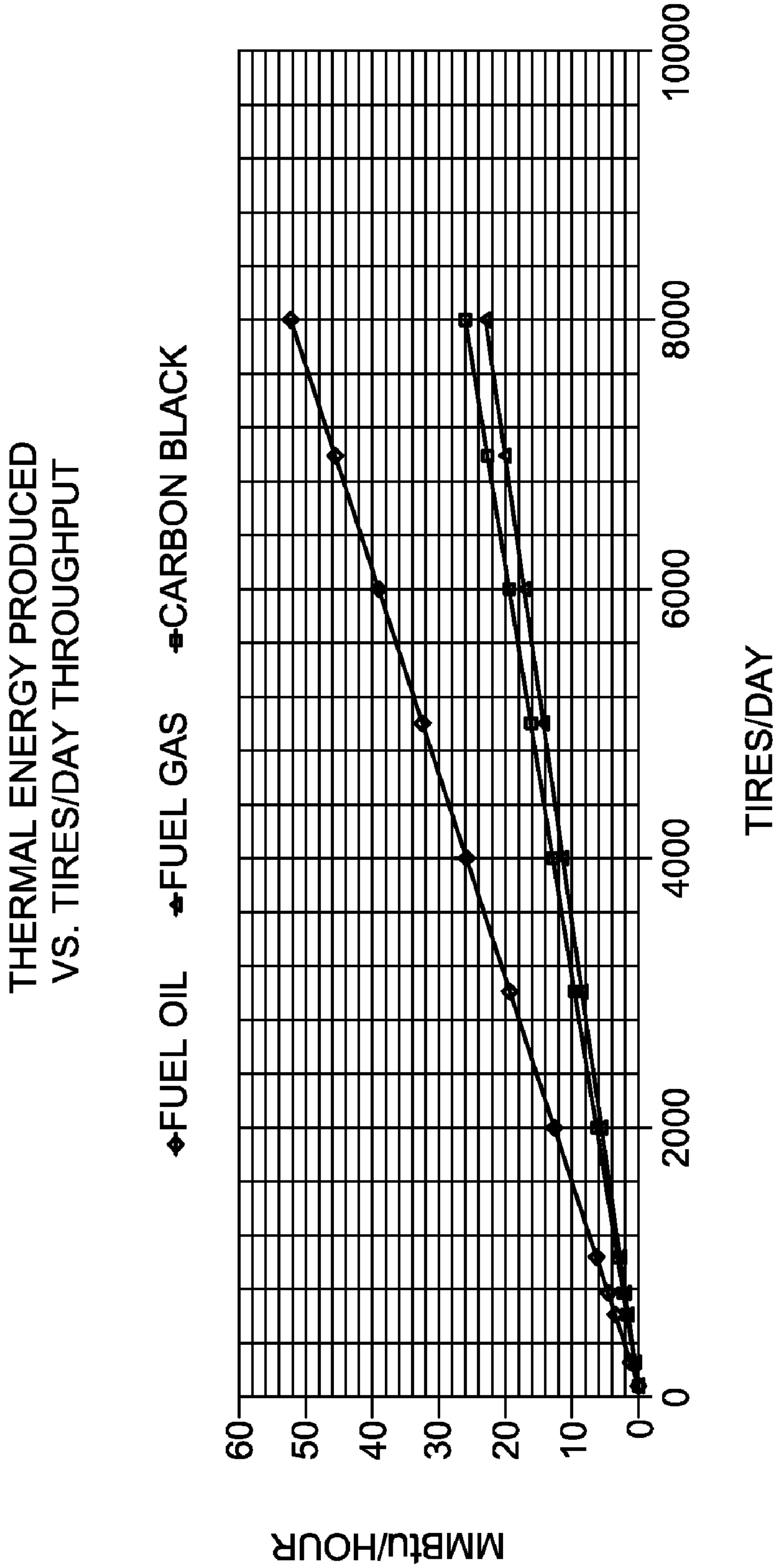
FIG. 9 is a graph illustrating the thermal energy recovered from scrap tire by-products of the prior art, at an applied microwave power, as illustrated in FIG. 7.
Figure 10:
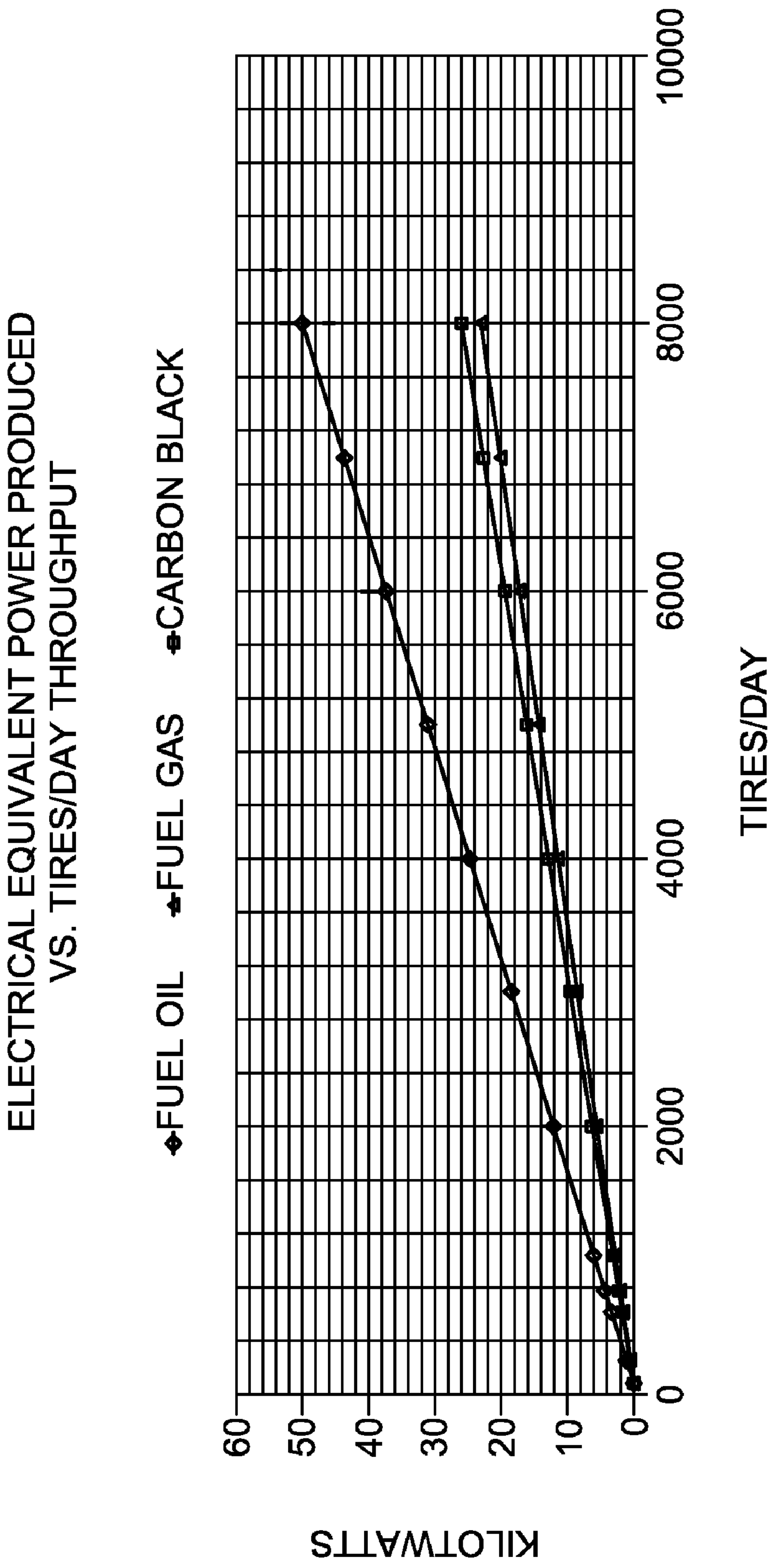
FIG. 10 is a prior art graph illustrating the equivalent electrical power produced from the thermal energy illustrated in FIG. 7 by an Internal Combustion Gas Turbine (ICGT), operating in simple cycle mode, at a combustion efficiency of only 35%.
Figure 11:
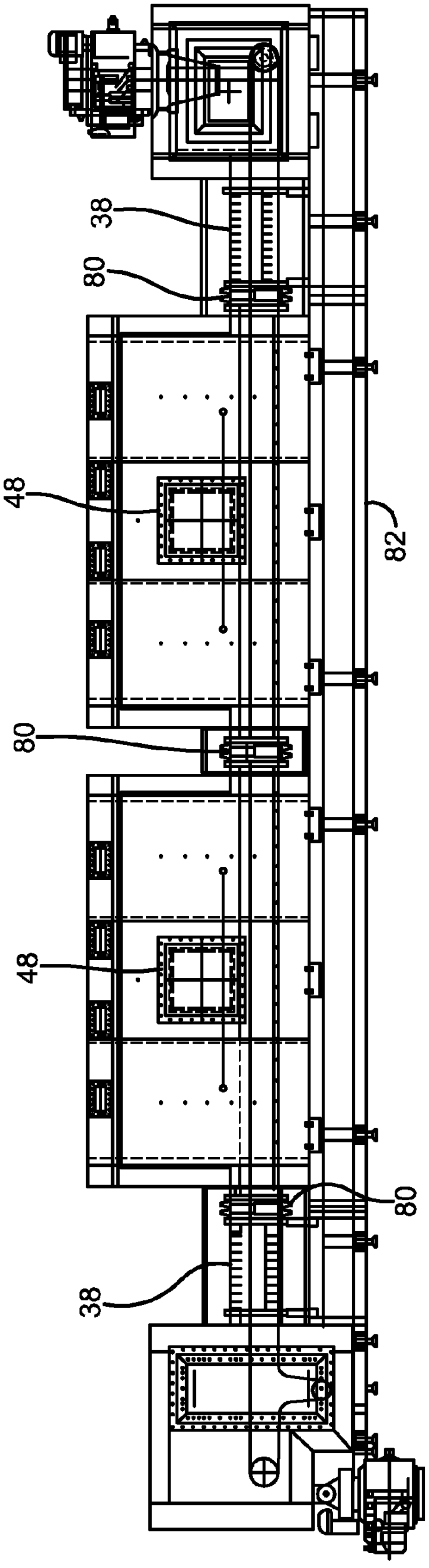
FIG. 11 is an elevation view of a two-module applicator assembly without waveguides.
Figure 12:
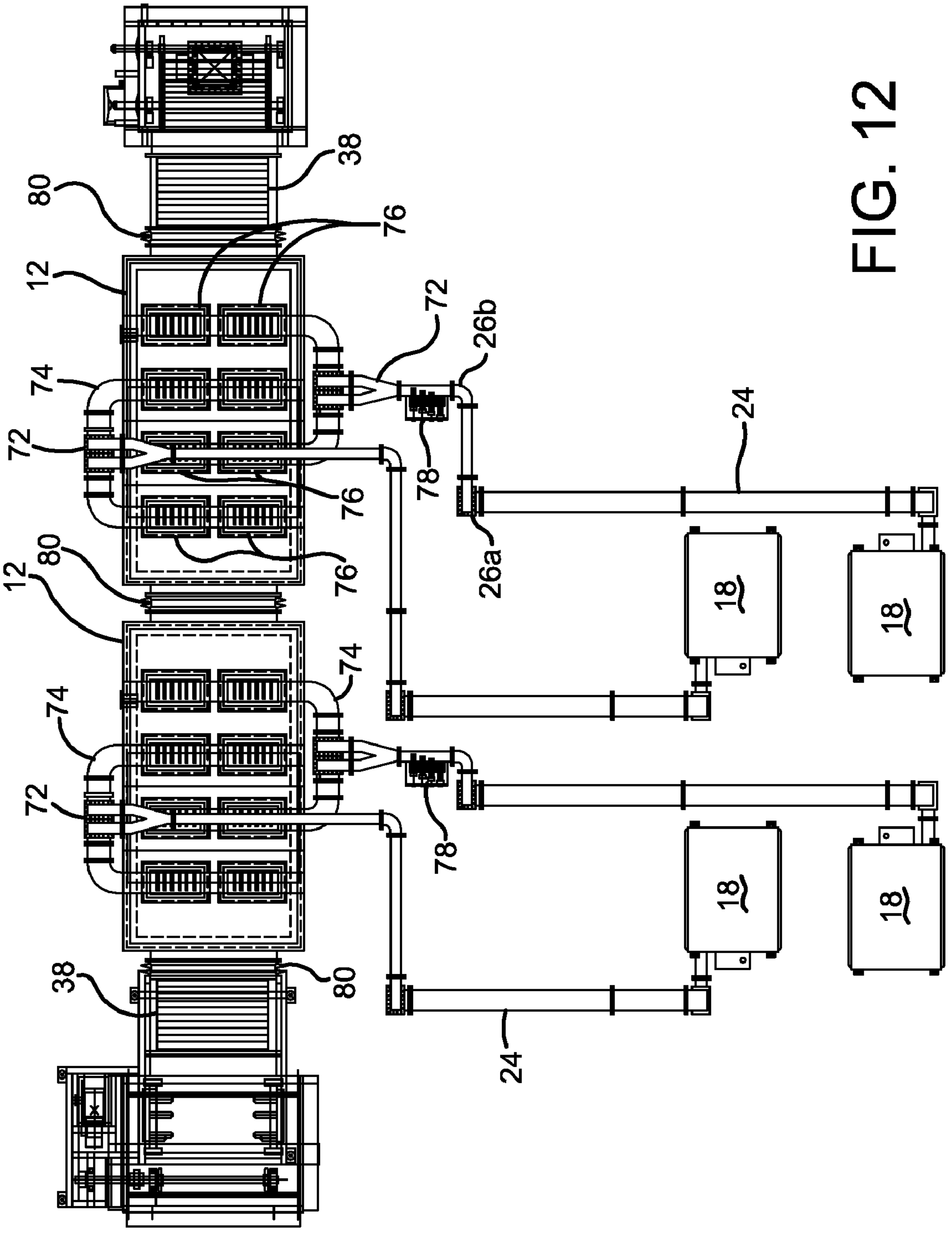
FIG. 12 is a plan view of two-module applicator assembly with waveguides.
Figure 13:
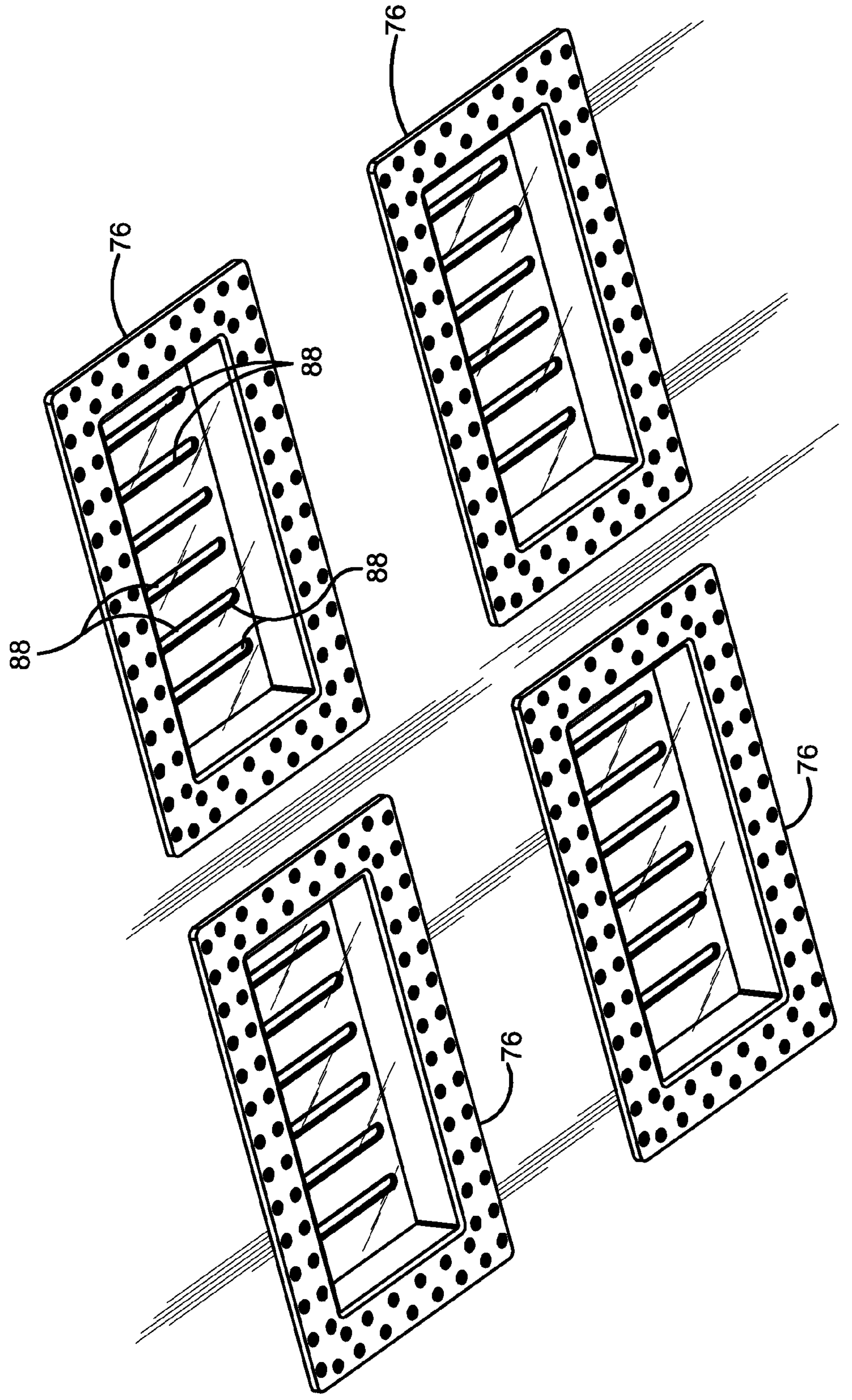
FIG. 13 is a perspective view of four applicator matrices.
Figure 14:
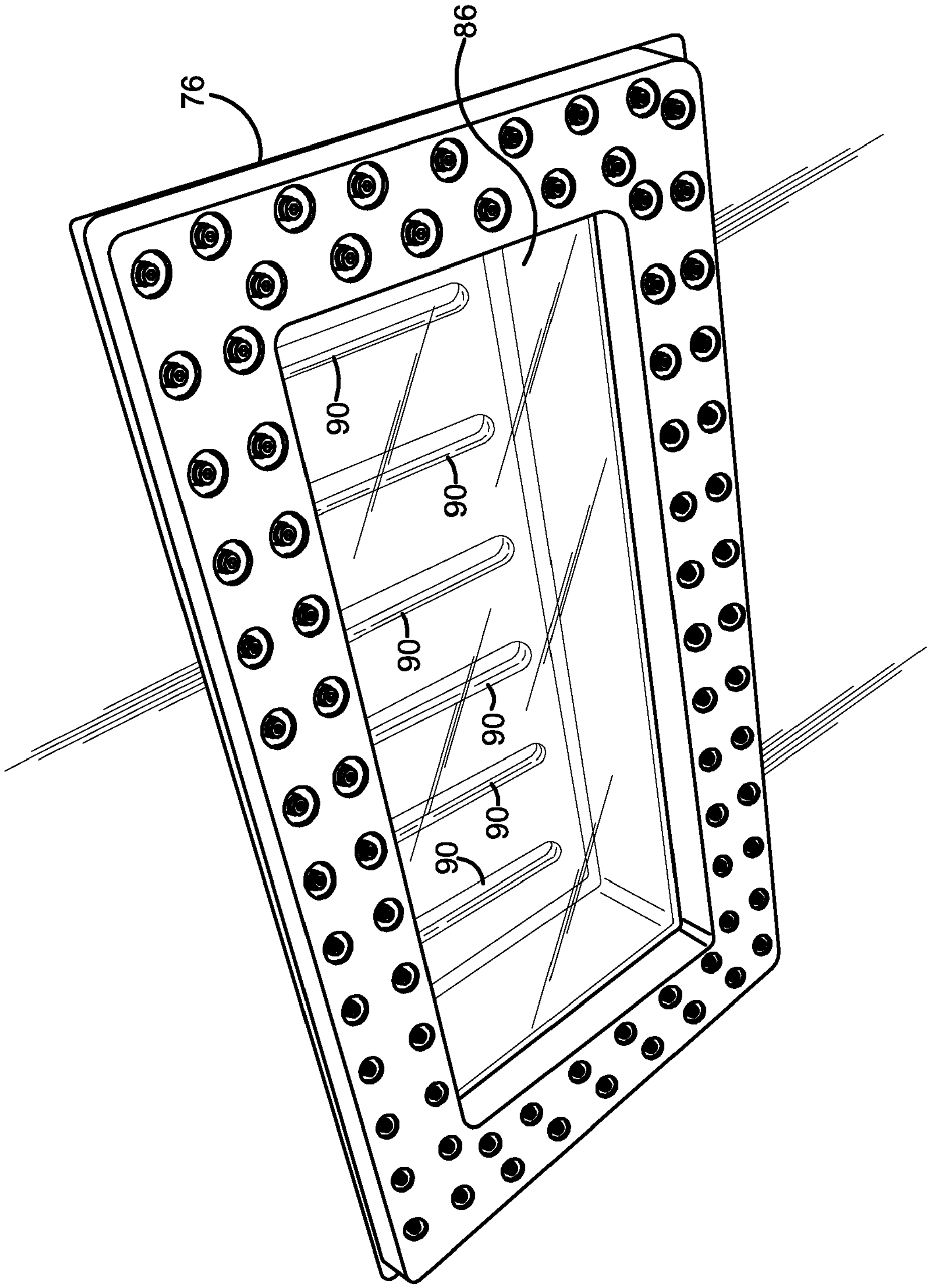
FIG. 14 is an enlarged perspective view of one applicator matrix of FIG. 13.
Figure 15A:
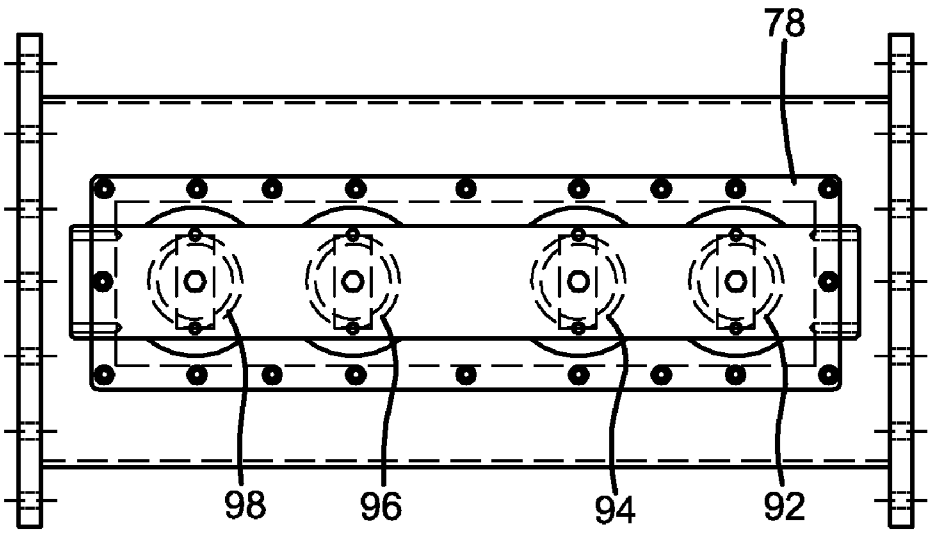
FIG. 15*a* is an enlarged side elevational view of a four-stage tuner illustrated in FIG. 12.
Figure 15B:
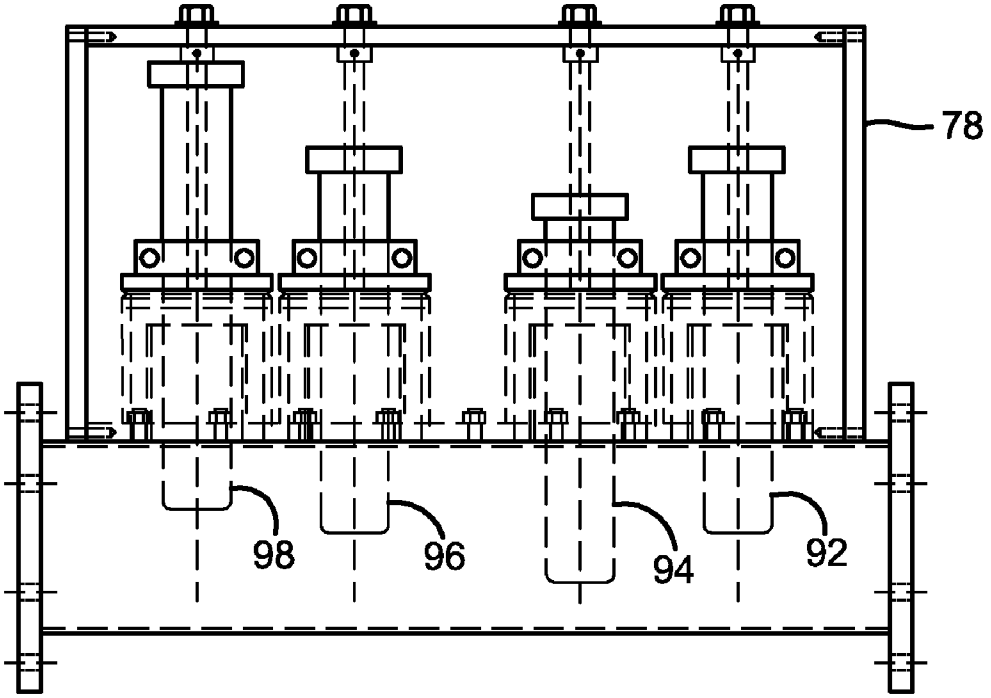
FIG. 15*b* is a bottom view of FIG. 15*a*.

These parametric process changes produced oil:gas ratios from ~10% Oil:90% Gas to ~90% Oil:10% Gas, The microwave test data in Table 2 provides an insight into the possible variations of output fuel (oil:gas) ratios from scrap tires. As the primary objective of the test was to maximize the production of high-Btu syngas, the majority of the test data exists at the oil:gas ratio of 25% Oil:75% Gas, Representative data points are given in Table 2, which illustrate process output fuel ratios throughout the ranges stated above. In addition, these data have been extrapolated for several variations of oil:gas ratios throughout the stated ranges, in order to produce the operating performance graphs illustrated in FIG. 7, FIG. 8, and FIG. 9. These graphs can be utilized to determine an indication of selected operating points.

At the elevated pressures, temperatures, and increased residence times, the amount of butane is significantly reduced, resulting in an increase in propane, and subsequently ethane. There were no olefins, arenes, or naphthenes present in the syngas produced. As a result of minimal olefins and aromatics in the hydrocarbon vapor stream before the condensor, the amount of oil is also minimal. Through monitoring of the syngas stream after the scrubber with a gas chromatograph, it is apparent that increased pressure within the applicator causes a direct effect on equilibrium temperature, gas residence time, but an inverse effect of the amount of butane.

The reduced amount of butane, and propane for that matter, in the syngas, provides a wider selection of commercially available Internal Combustion Gas Turbines (ICGT's) for combustion of the syngas. The high-Btu syngas heat value and its relation to a choice of an ICGT is only an issue if the syngas application is gas production or cogeneration of electricity. For sales gas purposes, recovery of the butane and propane from the syngas provides an additional revenue stream for the client. Regardless of the application, increasing the residence time in the applicator is a more cost-effective method to reduce the butane and propane, than to incorporate a gas stripper system in the microwave-based tire reduction process.

The conclusions concerning applicator pressure effects on temperature and hydrocarbon vapor residence time, along with types of by-products formed, were confirmed by a four-channel Gas Chromatograph (GC), employing a dual oven, with two (2) Flame Ionization Detectors, (FID), one (1) Thermal Conductivity Detector (TCD), and one (1) Electron Capture Detector (ECD). Separate 100-meter capillary columns were installed in each oven. The gas chromatograph carrier gas was high-purity hydrogen ($H_2$). Adjustable pressure reducing regulators with pressure gauges, were installed on all gas cylinders. Stainless Steel, Type 304, tubing was installed between the gas ports on the applicator and the gas chromatograph.

The applicator contained dual inlet ports for purge gas high-purity nitrogen ($N_2$), and one inlet port each for high-purity hydrogen ($H_2$) (reducing gas), and plasma enhancing/purge gas high-purity argon (Ar). A direct-reading bubble-type flowmeter was installed on the applicator at the purge gas inlet and a turbine-type mass flowmeter was installed in the applicator exhaust gas outlet piping after the discharge valve.

Other tests that were conducted, using this same microwave reduction system, included utilization of nickel (Ni), platinum/molybdenum (Pt/Mo), and zeolite catalysts to observe the enhanced reduction of the heavier hydrocarbons contained in the hydrocarbon vapor stream. In another series of tests, Argon was introduced into the applicator to observe the highly, energetic reactions created by the microwave-generated plasma. Catalytic conversion, plasma generation, and free-radical reduction of organic compounds through microwave excitation, will be addressed separately. Microwave-generated plasma in conjunction with catalyst-enhanced reduction resulted in increased product yields of syngas, with characteristics more similar to natural gas than process gas, with improved efficiency.

TABLE 2

Shredded Scrap Tire Reduction Test Results at 2450 MHz

| Test No. | Initial Mass (lbs) | Final Mass (lbs) | Mass Change (lbs) | Mass of Oil (lbs) | % Oil | Mass of Gas (lbs) | % Gas | MW Pwr. (kW) | Total Time (hr) | kW-hr/Tire |
|---|---|---|---|---|---|---|---|---|---|---|
| 1 | 7.998 | 6.614 | 1.384 | 0.327 | 23.63 | 1.057 | 76.37 | 6.6 | 1.912 | 1.58 |
| 2 | 10.000 | 8.102 | 1.898 | 0.794 | 41.83 | 1.104 | 58.17 | 8.2 | 1.833 | 1.50 |
| 3 | 10.163 | 8.201 | 1.962 | 0.576 | 29.36 | 1.386 | 70.64 | 9.0 | 1.750 | 1.55 |
| 4 | 8.579 | 6.693 | 1.885 | 0.316 | 16.76 | 1.569 | 83.24 | 9.0 | 2.133 | 2.24 |
| 5 | 8.512 | 6.449 | 2.063 | 0.325 | 15.75 | 1.738 | 84.25 | 9.0 | 2.133 | 2.26 |
| 6 | 8.823 | 7.013 | 1.810 | 0.472 | 26.08 | 1.338 | 73.92 | 9.0 | 2.133 | 2.18 |
| 7 | 8.538 | 6.761 | 1.777 | 0.391 | 22.00 | 1.386 | 78.00 | 9.0 | 2.133 | 2.25 |
| 8 | 8.818 | 6.815 | 2.003 | 0.326 | 16.28 | 1.681 | 83.92 | 9.0 | 2.133 | 2.18 |
| 9 | 7.716 | 6.566 | 1.150 | 0.661 | 57.48 | 0.489 | 42.52 | 9.0 | 3.000 | 3.50 |
| 10 | 7.716 | 6.435 | 1.281 | 0.111 | 8.67 | 1.170 | 91.33 | 9.0 | 3.500 | 4.08 |
| 11 | 9.987 | 8.461 | 1.526 | 0.549 | 35.98 | 0.977 | 64.02 | 9.0 | 2.133 | 1.92 |
| 12 | 15.625 | 12.523 | 3.102 | 0.782 | 25.21 | 2.320 | 74.49 | 9.0 | 3.500 | 2.02 |
| 13 | 20.568 | 14.507 | 6.061 | 1.068 | 17.62 | 4.993 | 82.38 | 9.0 | 4.000 | 1.75 |
| 14 | 20.552 | 14.838 | 5.714 | 1.155 | 20.21 | 4.559 | 79.79 | 9.0 | 4.000 | 1.75 |
| 15 | 13.228 | 12.162 | 1.066 | 0.319 | 29.92 | 0.746 | 69.98 | 9.0 | 2.217 | 1.51 |
| 16 | 13.228 | 12.264 | 0.964 | 0.204 | 21.16 | 0.760 | 78.84 | 9.0 | 2.167 | 1.47 |

TABLE 2-continued

Shredded Scrap Tire Reduction Test Results at 2450 MHz

| Test No. | Initial Mass (lbs) | Final Mass (lbs) | Mass Change (lbs) | Mass of Oil (lbs) | % Oil | Mass of Gas (lbs) | % Gas | MW Pwr. (kW) | Total Time (hr) | kW-hr/ Tire |
|---|---|---|---|---|---|---|---|---|---|---|
| 17 | 4.409 | 3.773 | 0.636 | 0.361 | 56.76 | 0.275 | 43.24 | 9.0 | 3.333 | 6.80 |
| 18 | 8.818 | 6.309 | 2.509 | 0.604 | 24.07 | 1.905 | 75.93 | 9.0 | 3.333 | 3.40 |
| 19 | 4.409 | 3.767 | 0.642 | 0.305 | 47.51 | 0.337 | 52.49 | 9.0 | 3.667 | 3.05 |
| 20 | 8.818 | 6.342 | 2.476 | 0.514 | 20.76 | 1.962 | 79.24 | 9.0 | 3.667 | 3.74 |
| 21 | 4.409 | 4.089 | 0.320 | 0.249 | 77.81 | 0.071 | 22.19 | 9.0 | 3.667 | 7.49 |
| 22 | 8.818 | 6.493 | 2.325 | 0.395 | 16.99 | 1.930 | 83.01 | 9.0 | 3.667 | 3.74 |
| 23 | 13.228 | 9.725 | 3.503 | 0.837 | 23.89 | 2.666 | 76.11 | 9.0 | 3.667 | 2.49 |
| 24 | 13.228 | 11.220 | 2.008 | 0.571 | 28.44 | 1.437 | 71.56 | 9.0 | 2.500 | 1.70 |
| 25 | 13.228 | 11.526 | 1.702 | 0.551 | 32.37 | 1.151 | 67.63 | 9.0 | 2.500 | 1.70 |
| 26 | 9.913 | 6.946 | 2.967 | 0.823 | 27.72 | 2.146 | 72.28 | 9.0 | 2.500 | 2.27 |
| 27 | 10.582 | 7.192 | 3.390 | 0.905 | 26.70 | 2.484 | 73.30 | 9.0 | 2.500 | 2.13 |
| 28 | 10.582 | 7.388 | 3.194 | 0.751 | 23.50 | 2.444 | 76.50 | 9.0 | 2.500 | 2.13 |

Increasing both the temperature from (572° F.→680° F.) equivalently, (300° C.→360° C.) and the microwave power (375 kW→600 kW) using a residence time of ~285 ms, produces both a change in the composition as well as the BTU content of the gaseous constituent. The "revised" liquid fuel characteristics are similar to those of No. 2 diesel fuel. The magnetron efficiency must be a minimum of 88% to achieve the "revised" results. All measured experimental percentages are approximately +/−2%.

TABLE 3

Gas Ref. Conditions: 14.696 psia, 60° F. (15.6° C.)

Syngas and Liquid Fuel Analyses

| | Original (Avg.) | | Revised | |
|---|---|---|---|---|
| Gas Fuel Analysis: | wt. % | vol. % | wt. % | vol. % |
| Methane: | 15.86 | 30.984 | 27.04 | 42.132 |
| Ethane: | 32.15 | 33.511 | 50.43 | 41.924 |
| Propane: | 7.51 | 5.338 | 9.68 | 5.488 |
| i-Butane: | 1.16 | 0.626 | 0.07 | 0.030 |
| n-Butane: | 32.64 | 17.601 | 2.10 | 0.903 |
| Nitrogen: | 10.68 | 11.940 | 10.68 | 9.523 |

| Gas Characteristics: | Original (Avg.) | Revised | Units |
|---|---|---|---|
| Molecular Weight, MW: | 31.3189 | 24.9790 | — |
| Specific Gravity, SG: | 1.0812 | 0.8624 | — |
| Density, ρ: | 0.0817 | 0.0655 | lbs/ft$^3$ |
| Specific Volume, v: | 12.2429 | 15.2762 | ft$^3$/lb |
| Compressibility, Z: | 0.9895 | 0.9944 | — |
| Specific Heat, $C_p$: | 0.4233 | 0.4425 | Btu/lb-° F. |
| Specific Heat, $C_v$: | 0.3451 | 0.3524 | Btu/lb-° F. |
| Ratio of Specific Heats, k: | 1.2265 | 1.2557 | — |
| Heat Value, HHV: | 1,635 | 1,217 | Btu/ft$^3$ |
| Heat Value, LHV: | 1,498 | 1,336 | Btu/ft$^3$ |
| Gas Constant, R: | 60.397 | 69.586 | ft-$lb_f$/$lb_m$-°R. |

TABLE 3-continued

Gas Ref. Conditions: 14.696 psia, 60° F. (15.6° C.)

| Liquid Fuel Analysis | | |
|---|---|---|
| Cetane Index (ASTM D613) | 25 | |
| Viscosity @ 40° C. (ASTM D445) | 1.2 | cst |
| Specific Gravity (ASTM 4052) | 0.89 | |
| API Gravity @ 60° C. (ASTM 4052) | 33.4 | |
| Initial Boiling Point (ASTM D86) | 63° | C. |
| 50% st. Boiling Point (ASTM D86) | 186° | C. |
| Final Boiling Point (ASTM D86) | 347° | C. |
| Elemental Iron Content (ASTM D3605) | 2 | ppm |
| Elemental Sodium Content (ASTM D3605) | 2 | ppm |
| Elemental Silicon Content (ASTM D3605) | 180 | ppm |
| Other Trace Metals Content (ASTM D3605) | <1 | ppm |
| Sulfur Content: (ASTM D1552) | 0.48 | wt. % |
| Carbon Residue Content (ASTM D524) | <0.01 | wt. % |
| Ash Content: (ASTM D482) | <0.007 | wt. % |
| Copper Strip Corrosion: (ASTM D130) | 2 | |

A comparison of the original average tire performance data with "original" average gas data and "revised" gas data is provided in Table 4 below.

TABLE 4

Comparison of Tire Performance Data Based on Average and Revised Gas Analyses

| Process Parameter (60:40 Oil:Gas) | Units | Avg. Gas (60:40) | Rev. Gas (69:31) | Avg. Gas (60:40) | Rev. Gas 69:31) |
|---|---|---|---|---|---|
| | | Demo Unit - Gas Analysis at 14.696 psia, 60° F. | | | |
| Scrap Tire Feedstock: | Tires/day | 20 | 20 | 6,000 | 6,000 |
| Total Operating Hours/Day | Hours | 1 | 1 | 24 | 24 |
| Total Mass Flow: | lbs/min | 6.667 | 6.667 | 83.333 | 83.333 |
| Total Heat Value (15,500 Btu/lb) | MMBtu/hr | 6.200 | 6.200 | 77.500 | 77.500 |
| Gaseous Fuel (40% Wt.): | | Gas Sample (avg.) with 10.68 wt. % Nitrogen | | | |
| Hydrocarbons (HC) + $N_2$: | lbs/min | 1.772 | 1.375 | 22.144 | 17.189 |
| Nitrogen ($N_2$) Mass Flow | lbs/min | 0.189 | 0.147 | 2.365 | 1.836 |
| HC Mass Flow - ($H_2S$, HCl, HBr): | lbs/min | 1.583 | 1.228 | 19.779 | 15.353 |
| Total Volumetric Flow: | ft$^3$/min | 21.688 | 21.007 | 271.11 | 262.58 |
| Specific Volume: | ft$^3$/lb | 12.243 | 15.276 | 12.243 | 15.276 |

TABLE 4-continued

Comparison of Tire Performance Data Based on Average and Revised Gas Analyses

| Process Parameter (60:40 Oil:Gas) | Units | Avg. Gas (60:40) | Rev. Gas (69:31) | Avg. Gas (60:40) | Rev. Gas 69:31) |
|---|---|---|---|---|---|
| Volumetric Heat Value (HHV): | Btu/$ft^3$ | 1,635 | 1,336 | 1,635 | 1,336 |
| Volumetric Heat Value (LHV): | Btu/$ft^3$ | 1,498 | 1,217 | 1,498 | 1,217 |
| Total Heat Value (HHV): | MMBtu/hr | 2.128 | 1.684 | 26.601 | 21.049 |
| Total Heat Value (LHV): | MMBtu/hr | 1.949 | 1.534 | 24.359 | 19.181 |
| Gas Fuel Equiv. Elect. Pwr. (LHV): | kW | 191 | 150 | 2,388 | 1,880 |
| $H_2S$ Gas to Liquid Scrubber: | | | | | |
| Total Mass Flow ($H_2S$): | lbs/min | 0.0124 | 0.0124 | 0.1554 | 0.1554 |
| Total Volumetric Flow: | $ft^3$/min | 0.1407 | 0.1893 | 1.7633 | 1.7633 |
| Specific Volume: | $ft^3$/lb | 11.347 | 15.265 | 11.347 | 15.265 |
| Volumetric Heat Value$_{MIXTURE}$ (HHV): | Btu/$ft^3$ | 1,633 | 1,334 | 1,633 | 1,334 |
| Volumetric Heat Value$_{MIXTURE}$ (LHV): | Btu/$ft^3$ | 1,496 | 1,215 | 1,496 | 1,217 |
| Total Heat Value (HHV): | MMBtu/hr | 0.0138 | 0.1515 | 0.1668 | 0.1411 |
| Total Heat Value (LHV): | MMBtu/hr | 0.0126 | 0.1380 | 0.1528 | 0.1288 |
| Residual Hydrogen Sulfide: | ppm$_{wt.}$/min. | 1.24 (1.24 × $10^{-6}$ lb/min) | | 15.54 | 15.54 |
| Other Gases to Scrubber: | | | | | |
| Total Mass Flow (HCl): | lbs/min | 0.000470 | | 0.0058 | 0.0058 |
| Total Volumetric Flow: | $ft^3$/min | 0.00499 | | 0.0615 | 0.0615 |
| Specific Volume: | $ft^3$/lb | 10.607 | | 10.607 | 10.607 |
| Residual Hydrogen Chloride: | ppm$_{wt.}$/min | 0.047 (0.047 × $10^{-6}$ lbs/min) | | 0.58 | 0.58 |
| Total Mass Flow: (HBr): | lbs/min | 0.0042 | | 0.0523 | 0.0523 |
| Total Volumetric Flow: | $ft^3$/min | 0.0201 | | 0.2500 | 0.2500 |
| Specific Volume: | $ft^3$/lb | 4.780 | | 4.780 | 4.780 |
| Residual Hydrogen Bromide: | ppm$_{wt.}$/min | 0.42 (0.42 × $10^{-6}$ lbs/min) | | 5.23 | 5.23 |
| Liquid Fuel (60% Wt): | | | | | |
| Total Mass Flow: | lbs/min | 2.390 | 2.747 | 29.876 | 34.333 |
| Heat Value (HHV): | Btu/lb | 19,600 | 19,600 | 19,600 | 19,600 |
| Total Heating Value (HHV): | MMBtu/hr | 2.811 | 3.230 | 35.134 | 40.375 |
| Liq. Fuel Equiv. Elect. Pwr (HHV): | kW | 275 | 317 | 3,444 | 3,957 |
| Total Gas/Liquid Fuels: | | | | | |
| Total Heat Value (Gas + Liquid) | MMBtu/hr | 4.759 | 4.764 | 59.494 | 59.556 |
| Total Elect. Equiv. (÷3411.8 kW/Btu) | kW | 1,395 | 1,396 | 17,440 | 17,456 |
| Scrap Tire Feedstock: | Tires/day | 20 | 20 | 6,000 | 6,000 |
| Total Operating Hours/Day | Hours | 1 | 1 | 24 | 24 |
| Elect. Pwr. Generation Summary: | | | | | |
| Electrical Power - ICGT: (×0.35) | kW | 488 | 489 | 6,104 | 6,018 |
| Elect. Pwr - Gen. Out.: (×0.985 × 0.97) | kW | 466 | 467 | 5,832 | 5,837 |
| Liq. Fuel Equivalent Elect. Power | kW | 275 | 317 | 3,444 | 3,957 |
| Gas Fuel Equivalent Elect. Power: | kW | 191 | 150 | 2,388 | 1,880 |
| Microwave Power to Process: | kW | 30.16 | 35.26 | 377.06 | 440.79 |
| Elect Pwr Req'd by Microwave: (÷0.88) | kW | 34.27 | 40.07 | 428.48 | 500.90 |
| Ancillary Losses: | | | | | |
| Less Elect. Pwr - $N_2$ Gen.: | kW | 11.19 | 11.19 | 22.38 | 22.38 |
| Less Elect. Pwr - Scrubber: | kW | 1.12 | 1.12 | 2.24 | 2.24 |
| Less Elect. Pwr - Chiller (Mag/P.S./CND): | kW | 9.12 | 9.12 | 80.55 | 85.87 |
| Total Ancillary Loads: | kW | 21.43 | 21.43 | 105.17 | 110.49 |
| MW Power Requirement: | kW | 34.27 | 40.07 | 428.48 | 500.90 |
| Total Elect. Pwr. Req'd. | kW | 55.70 | 61.50 | 533.65 | 611.39 |
| Net Electrical Power for Export: | kW (Gas Fuel) | +135 | +88.5 | +1,854 | +1,269 |
| Other By-Products: Carbon/Carbon Black/MOF Mixture: | | | | | |
| CB w/Metal Oxides, Fillers (MOF's): | lbs/min | 1.913 | 1.913 | 23.915 | 23.915 |
| Metal Oxides, Fillers (MOF's): | lbs/min | 0.289 | 0.289 | 3.618 | 3.618 |
| Net Carbon Black: | lbs/min | 1.624 | 1.624 | 20.297 | 20.297 |
| Carb. Black Ht. Value (14,096 Btu/lb) | MMBtu/hr | 1.374 | 1.374 | 17.166 | 17.166 |
| Other By-Products: Steel: | | | | | |
| Plated High-Carbon Steel: | lbs/min | 0.770 | 0.770 | 9.625 | 9.625 |
| Energy Balance: | | | | | |
| Tire Feedstock: | MMBtu/hr | 6.200 | 6.200 | 77.500 | 77.500 |
| Less Carbon Black: | MMBtu/hr | 1.374 | 1.374 | 17.166 | 17.166 |
| Less Liquid Fuel: | MMBtu/hr | 2.811 | 3.230 | 35.134 | 40.375 |
| Less Gaseous Fuel$_{LHV}$: | MMBtu/hr | 1.949 | 1.534 | 24.359 | 19.181 |
| Less Hydrogen Sulfide$_{LHV}$: | MMBtu/hr | 0.013 | 0.014 | 0.153 | 0.128 |
| Total Energy Recovered: | MMBtu/hr | 6.147 | 6.152 | 76.812 | 76.850 |
| Net Energy Difference: | MMBtu/hr | −0.053 | −0.048 | −0.688 | −0.650 |

TABLE 4-continued

Comparison of Tire Performance Data Based on Average and Revised Gas Analyses

| Process Parameter (60:40 Oil:Gas) | Units | Avg. Gas (60:40) | Rev. Gas (69:31) | Avg. Gas (60:40) | Rev. Gas 69:31) |
|---|---|---|---|---|---|
| MMBtu/hr × 293.1 × 0.35 × 0.985 × 0.97 = | kW equiv. | −5.195 | −4.705 | 67.434 | 63.710 |
| | % Difference | −0.85 | −0.77 | −0.90 | −0.84 |
| Magnetron Heat Load (12%): | Btu/hr | 14,022 | 16,411 | 175,435 | 205,083 |
| Control Panel Heat Load [P.S] (10%): | Btu/hr | 12,991 | 15,190 | 162,432 | 189,886 |
| Gas Condensor Heat Load ($Q\Delta TC_p$): | Btu/hr | 24,365 | 22,634 | 298,072 | 282,948 |
| Total Heat Load: | Btu/hr | 51,378 | 54.235 | 635,939 | 677,917 |

When the invention is used in the reduction mode, it is envisioned that both decrosslinking, depropagation, and depolymerization reactions are contemplated and within the scope of this invention. In one such embodiment, waste organic materials, such as scrap tires, are gasified by the continuous application of high power density microwave energy, using a continuous, self-aligning, stainless steel belt with 4 inches (10.16 cm) material retaining sides to produce stable by-products, which includes essentially ethane and methane.

When the invention is used in this mode, a process is provided for the recovery of specified gaseous products and includes maintaining the hydrocarbon vapor stream at least as high as an equilibrium temperature, above which the specified products are thermodynamically favored, followed by rapidly cooling the hydrocarbon vapor stream to a temperature at which the specified products are stabilized.

When gasifying shredded scrap tires, the preferred gaseous product is a hydrocarbon vapor stream, which consists of substantially ethane and methane in a ratio of two parts ethane to one part methane by weight plus 10% by weight nitrogen. A product stream, which varies from the preferred range, but is still acceptable, includes ethane, methane, and propane, at two parts ethane, to one part each of methane and propane, in addition to 10% by weight nitrogen. Another product stream, which varies further from the preferred range, but is also acceptable, includes ethane, butane, methane, and propane, at two parts each of ethane and butane to one part methane, and one part propane by weight, in addition to 10% by weight of nitrogen. Mixtures of ethane/methane, as well as those also containing propane and butane, have very high heat values, even when diluted with 10% nitrogen by weight, but can be directly injected into some ICGT combustion chambers without further treatment.

Conditions within the microwave applicator are selected so as to produce the desired components or gas:oil ratio in the hydrocarbon vapor stream. In a preferred embodiment, no liquid products, e.g., oils, will be produced. In order to insure that a 2:1 ratio of ethane:methane is produced, the feed rate, residence time, power density, energy level from the magnetrons is controlled as well as the pressure and temperature within the applicator.

In a typical scrap rubber tire reduction case, the following conditions will produce the desired ethane:methane mixture. The preferred applicator will contain anywhere from 3 to 10 microwave chambers, preferably six (6) magnetrons, each magnetron operating at about 915 MHz. Under these conditions, at steady-state operation, a residence time of approximately 285 milliseconds in the applicator, will result in a temperature in the applicator of about 680° F. (360° C.). Typically, the process pressure within the applicator will range from 0.1 to 0.5 psig (0.69–3.45 kPa). As kinetics favor reactions below equilibrium, the intermediate reactions release free hydrogen, which furthers the reduction of more complex organic molecules, leading to further breakdown, and a higher rate of reduction. The chemical reactions are exothermic in nature.

For crosslinked styrene-butadiene rubbers (SBR), the production of gaseous products includes the initial depolymerization of the sulfur crosslinks, followed by the addition of further microwave energy over time, resulting in the depropagation and breakdown of the two main polymers to form the desired products. At temperatures above about 680° F. (360° C.), depending on the feedstock, thermodynamics favor methane and ethane over the original polymers or other polymers. Accordingly, once depropagation and depolymerization is complete by maintaining those temperatures and applying the requisite microwave energy over a period of time, the gas stream remains stable at the high temperature. Very rapid cooling will prevent repolymerization or recombination of the gas constituents. The hydrocarbon gas stream is then flash-cooled, preferably down to about 100° F. (38° C.), to stabilize the ethane and methane at the lower temperatures. The residence time of the gas stream in the applicator is controlled in large part by the total pressure imposed by the nitrogen purge gas and the pressure developed by the formation of the hydrocarbon gaseous products of reduction, in conjunction with the flow rate set by the eductor at the inlet of the gas scrubber. The hydrocarbon vapor stream is then scrubbed to remove hydrogen sulfide, hydrogen chloride, and hydrogen bromide gases, hereafter referred to as contaminants.

The hydrocarbon vapor stream is scrubbed of its contaminants by a dry-contact, top-fed packed tower, packed with limestone and dolomite, while maintaining the gas temperature above the equilibrium point. A compressor must be used to force the hydrocarbon vapor stream through the scrubbing tower. The clean hydrocarbon vapor stream then exits and is flash cooled in an aluminum air-to-air heat exchanger, with liquid nitrogen acting as the cooling medium. The dry scrubber removes approximately 95-97% of the contaminants.

Alternately, the hydrocarbon vapor stream is scrubbed of its contaminants, preferably by a gas-contact, liquid scrubber, containing a dilute, aqueous solution of sodium hydroxide (NaOH) and sodium hypochlorite (NaOCl). The liquid scrubber eliminates the requirement for a compressor, as the scrubber eductor effects a 6 inch (15.24 cm) vacuum on the hydrocarbon gas stream flowing at approximately 285 acfm (484.2 $m^3$/hr). The scrubber is designed with two 12 inch (30.48 cm) diameter towers, containing special packing to minimize the overall height. The entire scrubber system is manufactured from high-density polyethylene. The liquid scrubber removes 99.99% of the contaminants, requires less space, and is more cost-effective in regards to the consumable chemicals than the dry scrubber. The scrubber tank containing chemical solutions is mounted under the twin packed-towers to provide stability to the towers in the mobile version. Column height, diameter and chemical tank size is determined by the process gas equilibrium and the desired removal efficiency.

Control of the liquid scrubber with its blowdown, makeup, and scrubbing cycles, is accomplished by the same PLC program, used for control of the microwave reduction process. In the mobile version of the invention, the liquid scrubber is installed in the microwave generator trailer, forward of the microwave generators and power distribution center. In the mobile version of the invention, makeup water for this system is pumped from a water reservoir installed under the applicator on the applicator trailer. Regardless of which scrubber is used, the hydrocarbon vapor stream exits the applicator and passes through a multiple-pass, water-cooled water-to-air process gas condenser. The process gas condensor provides cooling and stabilization of the gaseous products, while allowing recovery of the oil products. Residence time in the condensor is sufficient to allow the oil forming reactions to go to completion, while permitting the lighter, paraffin gases to stabilize and be drawn to the liquid scrubber.

A blanketing or purge gas is often used, nitrogen and argon being the two preferred gases. This gas may be supplied through drilled orifices through the choke pins in each R.F. trap. Nitrogen is preferred due to its lower cost, but has the potential of reacting with aromatic gaseous products of reduction, such as benzene, toluene, xylene, etc. With precise control of the applied microwave power and hydrocarbon gas residence time, in order to achieve the necessary reduction, formation of nitro-arene compounds can be avoided. Nitrogen gas is provided by a nitrogen generator, which includes a compressor and molecular sieve to produce relatively high-purity (≧98% purity) nitrogen.

The nitrogen generator is backed up with eight standard nitrogen bottles, in the event of a failure, while also acting as a deluge system in the event of a fire in the applicator. In the mobile version of the invention, the complete nitrogen system is installed in the microwave generator trailer forward of the hydrocarbon vapor scrubber. Oxygen sensors are also installed in this trailer to warn of a nitrogen leak, to prevent asphyxiation due to displacement of the air by the nitrogen.

Alternately, argon can be used since it is an inert gas, but at a higher cost, although lowered accounts are typically required due to its higher molecular weight. When operating this invention in the plasma mode, argon is used as both the plasma gas and the blanketing gas, thereby eliminating the possible formation of unwanted nitrogen-arene products.

Although the 100 kW magnetrons operate at 92% efficiency, the remaining 8% manifests itself as heat. Rejection of this heat is accomplished by a water-air chiller, sized for up to six (6) microwave generators. With the replacement of the inductive (transformer-based) power supply system with the switched-mode power supply, total heat load is reduced. In the mobile version of the invention, the chiller is installed at the front of the microwave generator trailer, forward of the nitrogen generator system. In the mobile version of the invention, cooling water is pumped from a water reservoir, installed under the applicator on the applicator trailer, through the chiller system and back into the microwave generators in a closed-loop mode.

Power for the mobile version of the microwave reduction system, is provided by an onboard diesel electric generator, capable of generating 750 kW, which is the total load from the microwave generators totaling 600 kW of microwave energy, and the ancillary items, including the nitrogen generator system, liquid scrubber system, and chiller system. All pertinent electrical parameters regarding the diesel generator operation are displayed on a continuously updated LCD module, located on the front of the generator control panel. Fuel for the diesel electric generator is pumped from a day tank, installed under the forward section of the applicator on the applicator trailer.

As stated previously, this process is, by definition, non-pyrolytic; requiring no externally-applied heat and achieving the dissociation of scrap tires and other organic compounds through molecular excitation of the organic molecules solely through the application of high power density microwave energy. Further, again by definition, power density (Watts/cubic feet) equals the applied microwave power (Watts) simultaneously to the entire volume (cubic feet) of material within the applicator. Other factors influencing power density and subsequently the applicator design are the applied frequency, permittivity, microwave absorption characteristics, and the voltage breakdown of the material within the applicator.

Conversely, pyrolytic reduction, by definition is the use of externally-applied heat to achieve thermal decomposition of organic compounds in a reduced oxygen atmosphere and involves the following steps: (1) subjecting the material for reduction to high temperatures from an externally-applied heat source, consuming considerable amounts of energy; (2) processing the products of reduction, such as melted rubber, oil, and char, which required special handling for safety and transportation; and (3) combustion of reduction products at high temperatures in the range of 932-1,472° F. (500-800° C.), resulting in additional environmental issues, such as formation of dioxins and other carcinogens.

By comparison, the microwave dissociation or reduction process for organic compounds achieved by this present invention requires: (1) no externally-applied heat source and is energy efficient—pyrolysis processes are typically 35-40% efficient, while the microwave presented in this invention achieved an operating efficiency of 93.5%; (2) no further processing, special handling or safety and handling considerations; and (3) dissociation or molecular breakdown of organic compounds occurs without combustion attributable at least in part to the high power density microwave energy, thus avoiding any environmental issues—using only microwave energy, the operating temperature to achieve necessary dissociation occurs at the reduced temperature range of 680-716° F. (360-380° C.) due to the severe intermolecular stresses created by absorption of the applied microwave energy.

The invention uses primarily passive components to overcome the mechanical and electromechanical limitations of methods used previously, in particular utilizing phase shifting of the microwave energy wave, to accomplish an impedance mismatch and subsequent phase rotation of the microwave energy waveform at an applied microwave frequency of 915 MHz prior to its introduction to the applicator, which is developed further in this invention, and which is still initially accomplished by incorporating unequal lengths of waveguide between the microwave generators and the applicator.

This invention teaches an approach which effectively shortens the lengths of waveguide, thus allowing the microwave generators and applicator to be installed in closer proximity to each other, thereby reducing resistive losses through the waveguides, whose losses manifest themselves as heat and wasted energy as well as reducing the equipment footprint. As better illustrated in FIG. 12, the smaller footprint is manifested by employing four (4) microwave generators 18 which feed at least one applicator 12, preferably two (2) applicators, more preferably three (3) or more, although the upper limit is to be determined using sound engineering principles, two applicators being illustrated in FIG. 11. Microwaves are directed from microwave generator 18 to at least one microwave applicator 12 by various lengths of waveguides 24, optionally in combination with low-loss 90° H-plane waveguide elbow assembly 26*a* and low-loss 90° E-plane waveguide assembly 26*b* in communication with at least a pair of low-loss divaricated waveguide assemblies 72, balanced waveguide assembly 74 to at least a pair of microwave diffuser matrices 76, more preferably four (4) diffuser matrices (shown in FIG. 13), most preferably eight (8) diffuser matrices (shown in FIG. 12). Each waveguide assembly/microwave generator pair propagating microwaves which are out-of-phase with respect to each other, as described previously. In at least one waveguide assembly, is positioned at least one cascaded multiple-stage microwave tuner assembly 78, more fully described below.

In this aspect of the invention, a low-loss, phase-shifting, waveguide system downstream of divaricated waveguide assemblies 72 with reflector plates—i.e., low-loss "Y"-splitter, long-radius E-Plane 26*b* and H-Plane elbows 26*a*, a new waveguide material, e.g., aluminum 3003-H14 to further reduce waveguide assembly losses through improved conductivity. As illustrated at least in FIG. 13, the microwave generators are offset, resulting in unequal lengths of waveguides from the microwave generators to the input of the divaricated waveguide assemblies 72. Phase delay occurs upstream of the divaricated waveguide assemblies, which introduces phase rotation of the microwave energy waveform due to the unequal waveguide lengths. The reduced length of one (1) wavelength to one-half (½) wavelength from the entrance flange of the throat, along with the reduced waveguide entrance angle from 60° to 15°, to the balanced output waveguide sections of divaricated waveguide assembly. This results in a lower loss and elimination of reflected power. The length of the output straight waveguide sections of the divaricated waveguide assembly are identical lengths from the throat to the output flanges for balanced output presented to the new waveguide configuration to the application. All E-Plane and H-Plane elbows are of a long-radius design to reduce waveguide losses and reflected power throughout the relatively long distance from the microwave generators to the applicator input. The reflector plate at the end of the waveguide assembly provides an effective short circuit to stop further propagation of the microwave energy waveform. If the microwave energy is not diffused through the diffuser channels, reflected power will result. Proper adjustment of the multi-stage microwave tuner assembly will allow matching of the microwave generator output to the load or material within the applicator, resulting in elimination of reflected power.

In one aspect of the invention, a manually tuned, three-stage microwave tuner assembly may be employed in which each tuning stub set (i.e., stubs 1 & 2 as well as sets 2 & 3) are separated by only ⅛ waveguide wavelengths. However, preferred is a four-stage automated tuner assembly. In a most preferred embodiment, the tuning stubs are motor-driven with individual feedback loops to the Programmable Logic Controller (PLC) in the Main Control Panel. Increasing from a three-stage tuner assembly to a four-stage tuner more accurately matches the load/tuner combination, permitting the addition of automatic tuning for improved process operation. The automatic tuning assembly permits continuously-adjustable compensation to match the microwave generators to a changing load in the material within the applicator. Matching is achieved by controlling the amplitude of the reflection coefficient, while tandem or cascade movement controls the phase angle through a parameter known as susceptance. Susceptance within the waveguide section varies as the insertion depth and the selected diameter of the tuning slug, which results in controlling the amplitude of the reflection coefficient. For a four-stage tuner, stubs one 92 and three 96 control admittance, while stubs two 94 and four 98 control the conductance. Therefore, the reflection amplitude and phase angle can be varied with the tuner's adjustment range to achieve minimum net reflected power returning from the applicator. Tuning stubs 92 and 94 are separated by ¼ wavelength for optimum tuning effect. Tuning stubs 94 and 96 are separated by % waveguide wavelengths. Tuning stubs 96 and 98 are separated by ¼ waveguide wavelength. In this preferred embodiment, it is seen that there is an increased spatial distance between the first set of tuner stubs 92, 94 as compared to the second set of tuner stubs 96, 98, resulting in minimization (if not elimination) of interaction between the two sets of tuning stubs.

Low-loss divaricated waveguide assembly 72 directs microwaves to at least one, preferably a dual matrix of eight (8) microwave diffusion assemblies 76, a low-loss, sealed dual-flanged waveguide isolation assembly for each microwave diffuser, a balanced waveguide configuration 74 serving the eight inputs to each applicator 12 and a waveguide terminator at the end of the microwave diffuser assembly, and the multi-mode applicator itself.

The use of low-loss components provides less resistance in the waveguide assembly, leading to reduced reflected power, resulting in higher transfer of microwave energy from the microwave generators to the applicator. The typical reflected power in a conventional waveguide design at a power level of only 75 kW is approximately 6% or 4.5 kW. The measured reflected power in this invention operating at full power of 200 kW per applicator module, with the low-loss waveguide design, and all of the other low-loss enhancements is less than 0.1% or 1 kW max.

The microwave diffuser matrix contributes significantly to the low reflected power, in that the maximum amount of applied power can be coupled directly into the eight (8) diffuser modules per applicator through six (6) channels 90 per diffuser (illustrated with four assemblies in FIG. 13 and in exploded form in FIG. 14), each port having a curved (rounded) or radiused or curvilinear bevel 90, for a total of forty-eight (48) essentially parallel, applicator input channels in the diffuser matrix, with minimum losses and reflected power. Each channel is separated by a spacing equivalent to between 1-2 waveguide wavelengths, more preferably about 1.5 waveguide wavelength, each channel having no sharp contour edges. By this contour edge limitation, it is meant that the planar intersection does not approximate 90°.

In this application, it should be noted that the number of channels per diffuser module is dependent on various factors which include applicator size, port cross-sectional area, and distance of separation between channels, to prevent arcing within diffuser channels. For a 60 kW microwave generator, four (4) channels are generally sufficient. For a 75 kW microwave generator, generally five (5) channels would be employed, while for a 100 kW microwave generator, six (6) channels would be used.

As a guide to the above, it is noted that for an applicator which has eight (8) diffuser matrices, each with 4-channel diffusor/applicator=60 kW (120 kW total) dissipation per applicator, 10 feet (304.8 cm) in overall length, 4 feet (121.9 cm) wide and with an active height of 36 inches (91.4 cm). The channels may be widened, observing the applied microwave power to conform to the power density requirements of the channels, relative to the maximum input to the WR-975 waveguide.

For an applicator which has eight (8) diffuser matrices, each with 5-channel diffusor/applicator=75 kW (150 kW total) dissipation per applicator, 10 feet (304.8 cm) in overall length, 4 feet (121.9 cm) wide and with an active height of 39 inches (99.1 cm). The channels may be widened, observing the applied microwave power to conform to the power density requirements of the channels, relative to the maximum input to the WR-975 waveguide.

For an applicator which has eight (8) diffuser matrices, each with 6-channel diffusor/applicator=100 kW (200 kW total) dissipation per applicator, 12 feet (365.8 cm) in overall length, 4 feet (121.9 cm) wide, with an active height of 42 inches (106.7 cm).

More specifically, in one embodiment of the invention, the microwave applicator will have the following specifications as illustrated in Table 5.

TABLE 5

| microwave applicator specifications |
|---|
| Channel Length: 7¾ inches (19.7 cm) long |
| Channel Width: ½ inch (1.27 cm) |
| Channel Cross-Sectional Area: 99.84 square inches (644.13 $cm^2$) |
| WR-975 Cross-Sectional Area: 95.06 square inches (613.29 $cm^2$) |
| Channel Entrance Angle: The channel entrance has a milled radius of 15/64 inch (0.60 cm). |
| Alternately, an entrance angle of 45° may be milled on the diffusor plate. |
| Channel Exit Angle: The channel exit has a milled radius of 15/64 inch (0.60 cm). |
| Alternately, an exit angle of 45° may be milled on the diffusor plate. |
| Channel Separation: ¾ waveguide wavelength |
| Number of Diffusor Channels per Generator Inputs to Applicator: 12 downstream of each output from the divaricated waveguide assembly. |
| Applicator Dimensions: 144 inches (365.8 cm) long × 72 inches (182.9 cm) wide × 60 (152.4 cm) inches high |
| Applicator Active Area: 144 inches (365.8 cm) long × 52 inches (132.1 cm) wide × 42 inches (106.7 cm) high |
| Applicator Volume: 314,496 cubic inches (5.15 $m^3$) |
| Material Depth: 2.75 inches (6.99 cm) |
| Material Volume: 20,592 cubic inches (0.34 $m^3$) |
| Volume Filling Factor: 6.55 |
| Power Density: 592.24 $kW/m^3$ |

The low-loss purged, sealed, dual-flanged waveguide isolation assembly between the microwave diffuser and the applicator input port contains two low-loss, dielectric wafers ⅜ inch (0.95 cm) thick with a low coefficient of thermal expansion to re-establish the focal point of the guided microwave wavepoint in the center of the waveguide. The dielectric wafers are inset within the flanges and connected by a quarter-wavelength long section of waveguide. The dielectric wafers were chosen according to the following criteria: (1) minimum impedance to the incoming waveform or maximum input admittance and propagation constant compensate for the permittivity of the wafer material in order to avoid dielectric heating; (2) minimum coefficient of thermal expansion to permit high differential temperatures on opposite sides of the assembly; and (3) minimum index of refraction for the incoming waveform to minimize refocusing efforts in accordance with Snell's law and the Brewster angle, relative to angles of incidence and reflection. Each wafer contains a conductive carbon gasket in a picture-frame configuration, to provide a conductive path from the waveguide to the flanges. The waveguide isolation assembly is nitrogen-filled to maintain an inert, non-flammable atmosphere within the assembly in the event of a failure of either wafer. The combined effects of the above results in maximum energy transfer of the microwave waveform into the applicator, while providing total isolation between the applicator and the generator. This is an important consideration when the applicator contains flammable or explosive gases.

An additional significant process improvement within the newly-designed, insulated, double-walled, applicator is a sealed, purged low-loss (high-conductivity) seamless aluminum cavity to reduce wall losses, plus the capability to operate at a maximum internal temperature of approximately 752° F. (400° C.). The temperature rating increases to 1500° F. (816° C.) when the applicator described in this invention is fabricated from Stainless Steel, Type 304. The multi-module applicator assembly also includes flexible expansion joints 80 and a floating base frame assembly 82 to allow compensate for thermal expansion and contraction during startup and shutdown operations, respectively as better illustrated in FIG. 11.

The cumulative effect of these improvements represents significant improvements in microwave efficiency, temperature distribution within the applicator assembly, and reduced energy consumption for materials processing, and total isolation of the process gases from the highly energetic atmosphere within the microwave generator. It is important to note that the combination of 4-stage tuner assembly 78, dual pressure window assembly 86 with nitrogen purge, microwave diffuser assembly 90, microwave diffuser matrix 76, and the microwave applicator waveguide geometry, namely the pair of divaricated waveguides are what form at least a portion of the improvement described in this invention.

Although all of the above contribute to significant improvements in efficiency and resulting increase in processed material (throughput), without being held to any one theory of operation, it is believed that the microwave diffuser matrix 76, consisting of eight (8) microwave diffusers, and the nitrogen-purged dual pressure window assemblies (preferably using quartz, zirconia or alumina windows), contribute a significant improvement to the invention.

However, for the ability to process various and different materials in this system, it should be recognized that the 4-stage tuner system allows a proper match between the microwave generator(s) and the material being processed (load). In this manner, the same product is capable of processing virtually any of the solid hydrocarbon materials we have identified; i.e., scrap tires, mixed plastics, automobile shredder residue (ASR), roofing shingles, construction/demolition waste, medical waste, municipal solid waste (MSW), and PCB/PAC/HCB-laden or fuel-laden soils and aggregates within the same applicator unit.

Although this invention is illustrated in a stationary configuration, it may be readily converted to a mobile configuration for transport to various processing locations.

The result of adjusting the control valve and observing its corresponding effects on pressure, temperature, and hydrocarbon residence time within the applicator are illustrated in Tables 5a and 5b, the tables being modified for English and Metric units. These parametric process changes directly affect the ratio of the oil:gas produced, and are also included in Tables 5a & 5b.

TABLE 5a

| Control Valve Operation and Effects on Process Parameters (U.S Units) | | | | | | | |
|---|---|---|---|---|---|---|---|
| Discharge Valve Opening % | Applicator Internal Pressure psig | Hydro-Carbon Gas Temp ° F. | Applicator Residence Time mS | Byproduct Flow Oil Flow lb/min | Oil/Gas Ratio Oil % | Oil/Gas Ratio Gas % | Gas Flow lb/min |
| 50.0 | 10.0 | 842 | 400 | 4.979 | 10 | 90 | 44.503 |
| 56.3 | 8.9 | 822 | 360 | 9.959 | 20 | 80 | 39.558 |
| 62.6 | 7.8 | 802 | 320 | 14.938 | 30 | 70 | 34.613 |
| 68.8 | 6.7 | 782 | 280 | 19.917 | 40 | 60 | 29.669 |
| 75.0 | 5.6 | 762 | 240 | 24.897 | 50 | 50 | 24.724 |
| 81.3 | 4.5 | 742 | 200 | 29.876 | 60 | 40 | 19.779 |
| 87.5 | 3.3 | 722 | 160 | 34.855 | 70 | 30 | 14.834 |
| 93.8 | 2.2 | 702 | 120 | 39.834 | 80 | 20 | 9.890 |
| 100.0 | 1.0 | 680 | 80 | 44.814 | 90 | 10 | 4.945 |

TABLE 5b

| Control Valve Operation and Effects on Process Parameters (Metric Units) | | | | | | | |
|---|---|---|---|---|---|---|---|
| Discharge Valve Opening % | Applicator Internal Pressure kPa | Hydro-Carbon Gas Temp ° C. | Applicator Residence Time mS | Byproduct Flow Oil Flow kg/min | Oil/Gas Ratio Oil % | Oil/Gas Ratio Gas % | Gas Flow kg/min |
| 50.0 | 68.9 | 450 | 400 | 2.258 | 10 | 90 | 20.186 |
| 56.3 | 61.4 | 439 | 360 | 4.517 | 20 | 80 | 17.943 |
| 62.6 | 53.8 | 428 | 320 | 6.776 | 30 | 70 | 15.700 |
| 68.8 | 46.2 | 417 | 280 | 9.034 | 40 | 60 | 13.458 |
| 75.0 | 38.6 | 406 | 240 | 11.293 | 50 | 50 | 11.215 |
| 81.3 | 31.0 | 394 | 200 | 13.552 | 60 | 40 | 8.972 |
| 87.5 | 22.8 | 383 | 160 | 15.810 | 70 | 30 | 6.729 |
| 93.8 | 15.2 | 372 | 120 | 18.068 | 80 | 20 | 4.486 |
| 100.0 | 6.9 | 360 | 80 | 20.327 | 90 | 10 | 2.243 |

The primary purpose of developing the above methods of operation is to reduce the Btu content or heat value, along with the molecular weight of the recovered gas in order to be able to inject it directly into the combustion chamber of a gas generator or gas turbine, readily available from multiple vendors. Previously, the high butane content resulted in a Btu value that was unacceptable to all manufacturers of gas generators and all but two gas turbine manufacturers. The solution was to increase the applied microwave power from 375 kW to 600 kW, thereby, increasing the operating temperature from 572° F. (300° C.) to 680° F. (360° C.). This resulted in an increase in applicator pressure from atmospheric pressure of slightly above 0 pounds per square inch gauge (psig) or approximately 14.696 pounds per square inch absolute (psia), to approximately 1.0 psig or 15.696 psia, causing a reduction in the residence time from 285 milliseconds to 80 milliseconds. It was also determined at the same time that the discharge valve could be throttled or closed in a controlled manner to raise the gas temperature, raise the applicator pressure and increase the hydrocarbon (HC) residence time.

Throttling of the discharge valve was accomplished with a standard 4-20 mA loop generated by the PLC, with a cascade temperature feedback control loop. In other words, as the discharge valve is closed, the temperature increases until the desired process temperature is reached and the valve is held at that position by the PLC. The operating temperature of 680° F. (360° C.) and 1 psig is the temperature and pressure observed to cause the majority of the butane (95%) to break down into approximately 55% methane and propylene and approximately 40% to break down into ethane and ethylene.

As the discharge valve is throttled or closed further, the temperature continues to increase along with the residence time. However, 842° F. (450° C.) was set as the upper limit to avoid coking or charring of the oil. In addition, the discharge valve must remain open at a minimum of 50%, as that is the minimum flow of hydrocarbon gas required for proper operation of the condensation and oil/gas separation system.

The practical upper limits of gas temperature, applicator pressure, and residence time of approximately 750° F., (399° C.) 5 psig, and 240 mS, respectively. These conditions are set with the discharge valve approximately 25% closed (75% open). When operating the process under these conditions, the practical maximum of butane and subsequently propane conversion to a lower Btu and molecular weight is achieved, along with a further increase in oil formation.

The chemical shift due to the increased microwave energy and effects of the throttle valve resulted in reducing the butane from 32.64% to 2.10%, but more importantly increased the propane from 7.51% to 9.68%, ethane from 32.15% to 50.43%, and the methane from 15.86% to 27.04%, resulting in an overall decrease in gas of approximately 9%, with a corresponding 9% increase in the oil formation. The oil increase is due to the formation of the olefins or oil-formers, ethylene and propylene. While the ethane:methane ratio remains at approximately 2:1, the Btu content has been reduced from 1,498 Btu/ft$^3$ to 1,217 Btu/ft$^3$, with a corresponding reduction in the molecular weight from 31.3189 to 24.9790. The new gas mixture may now be directly injected into the combustion chamber of any manufacturer's gas generator or gas turbine. Alternately, the gas mixture may be directly injected into the nation's natural gas transmission pipelines for direct distribution to industrial, commercial and residential customers.

The combined inclusion of the above improvements installed in the present invention microwave reduction system provides an overall efficiency increase from approximately 88% to approximately 90% in the initial testing of this current invention. These data are reflected in Table 6 in Tests 1 and 2. Further improvements in magnetron control electronics, power stabilization circuits, and fine tuning of the tuning adjustments stubs, resulted in an efficiency increase to over 94%. These data are reflected in Table 7 in Tests 3 and 4.

TABLE 6

| Prior Art Testing results | | | | | | |
|---|---|---|---|---|---|---|
| PARAMETERS MEASURED | TEST 1 | TEST 2 | TEST 3 | TEST 4 | TEST 5 | TEST 6 |
| Filament Current (A) | 105 | 100 | 95 | 90 | 85 | 70 |
| Filament Voltage (V) | 11.5 | 11.0 | 10.4 | 9.9 | 9.3 | 7.7 |
| Anode Voltage (kV) | 13.5 | 13.3 | 15.8 | 17.2 | 18.4 | 19.3 |
| Anode Current (A) | 2.5 | 3.0 | 4.0 | 4.5 | 5.0 | 6.0 |
| Magnet Current (A) | 3.7 | 3.7 | 4.3 | 4.7 | 5.0 | 5.1 |
| Microwave Output Power (Kw) | 30 | 35 | 55 | 68 | 82 | 102 |
| Efficiency (%) | 88.9 | 87.7 | 87.0 | 87.9 | 89.1 | 88.1 |

TABLE 7

| Performance of Current System | | | | |
|---|---|---|---|---|
| PARAMETERS MEASURED | TEST 1 | TEST 2 | TEST 3 | TEST 4 |
| Filament Current (A) | 69 | 69 | 69 | 69 |
| Filament Voltage (V) | 12.6 | 12.6 | 12.6 | 12.6 |
| Anode Voltage (kV) | 19.7 | 19.7 | 19.6 | 19.6 |
| Anode Current (A) | 5.60 | 5.65 | 5.51 | 5.41 |
| Magnet Current (A) | 5.95 | 5.95 | 6.25 | 6.25 |
| Microwave Output Power (kW) | 99 | 100 | 102 | 100 |
| Efficiency (%) | 89.7 | 89.8 | 94.5 | 94.3 |

Discussion

Without being held to one theory of operation, or one mode of performance, it is believed that the benefits of the invention are derived at least in part, by introducing microwave excitation of water molecules inside the organic material by subjecting the material to high frequency radio waves in the ultra-high frequency (UHF) band. The polar water molecules in the material attempt to align themselves with oscillating electric field at a frequency of 915 MHz or approximately every nanosecond, As the molecules cannot change their alignment synchronously with the changing electric field, the resistance to change manifests itself as heat, and the moisture trapped within the material is released as water vapor or steam. The heat conducted through the material and capillary action within the material converts any surface moisture to water vapor. This efficient release of moisture from the organic material reduces energy costs and increases throughput. In the case of non-polar molecules, the applied microwave energy is coupled to the entire volume of the material, resulting in dielectric polarization. Since a phase difference occurs between the applied electric field and the energy absorbed within the material, the losses within the material act as a resistance, resulting in additional heat generated within the material. The heat generated from dipolar and dielectric heating of the material is sufficient to effectively cause bond dissociation, generation of free radicals and hydrogen, resulting in the volumetric reduction of the material and formation of recoverable by products.

As the invention is designed for unattended, automatic operation, with a display in the customer's main control room, no additional operating personnel are needed. The use of this invention results in an immediate increase in process efficiency from 20-30% with incineration, 30-40% with pyrolysis, to over 85% with high-density microwave energy operating at 915 MHz, and to over 93.5% by employing the improvements described with the current invention, without any consideration for heat recovery.

However, in the case of tires, plastics, PCB's, e-waste (computer waste), roofing shingles, shale oil and bituminous coal, a phenomena known as thermal runaway, occurs due to the inability of these materials to dissipate the internal heat, caused by microwave excitation of polar and non-polar materials, sufficiently fast to their surroundings. Therefore, the increase in enthalpy is greater within the material than in the surrounding region. The internal temperature continues to increase at an even faster rate, and decomposition of the organic material subsequently occurs. When a high power density electric field is applied at 915 MHz, metal particles within the material separate, leading to a higher loss factor, particularly after decomposition begins, resulting in products of decomposition with an even higher loss factor. Since the loss factor is directly proportional to the power density and the rise in temperature, the material is subjected to even higher internal power dissipation. As carbon is one of the intermediate products of high-temperature decomposition by microwave reduction, and has a much higher loss factor than plastics or rubber, the higher temperature leads to even greater power dissipation within the material, leading to further molecular breakdown. Hydrogen released during the molecular breakdown and the thermal runaway phenomenon produce an intense series of exothermic reactions, until equilibrium occurs. Above equilibrium, thermodynamic control is favored.

Raw Material Particle Sizing Aspects

The starting material for this invention, as in the case of scrap tires, is typically in a random chunk form, a diameter or thickness, which typically varies from ½ inch (12.7 mm)×½ inch (12.7 mm) or smaller, to a maximum which does not typically exceed 2 inches (5.08 cm). This invention will also process material, which has been generated by a hammer mill, whose scrap tire material approaches 3 inches (7.62 cm) in size. The penetration depth of this material at 915 MHz is several inches, and the material retaining sides of the belt are 4 inches (10.16 cm) in height; therefore, the random raw material sizes, as provided by the scrap tire shredders and chippers, are acceptable.

An additional desirable aspect of the raw material is that the scrap tire material be subjected to a steel wire removal system. Though this step is not necessary for the proper operation of the invention, steel wire removal contributes to an additional 12-15% process efficiency for the microwave reduction system, which more than offsets the cost of the steel wire removal.

Contact Time

While not a primary metric for control, the material contact time of the material within the applicator is primarily dependent on the speed of the belt, which is controlled by a variable speed motor, which in a typical application will range from 1 to 8 feet per minute (0.305-2.44 meters per minute). Increasing the contact time within the applicator will increase the types of products; i.e., gas:oil ratio and composition of the hydrocarbon vapor stream. Increasing the contact time still further will result in bond breaking, leading to decrosslinking, or depropagation or depolymerization or all three, occurring either simultaneously or sequentially, dependent on the applied microwave power density and applicator pressure.

Waveguides

In a preferred embodiment, the waveguides will be low-loss divaricated waveguide assemblies 72 which direct out-of-phase microwaves into at least one pair, preferably a matrix of eight (8) microwave diffusion assemblies per applicator, in combination with a low-loss, sealed dual-flanged waveguide isolation assembly for each microwave diffuser, a balanced waveguide configuration 74 serving the eight inputs to each applicator 12 and a waveguide terminator at the end of the microwave diffuser assembly, and the multi-mode applicator itself. Due to the presence of the nitrogen or argon, higher microwave power density can be applied to the applicator, as nitrogen and argon significantly raise the voltage breakdown point. Further, nitrogen and argon serve as a blanketing or purge gas within the waveguide, in the event of failure of the pressurized fused quartz, dual window assembly (although other materials such as zirconia and alumina may be used as a substitute for quartz).

Microwave Frequency

Historically, the frequency of 915 MHz was not originally allocated for use in the Industrial, Scientific, and Medical (ISM) applications throughout the world, and no allocation for 915 MHz applications exist today in continental Europe. However, in the United Kingdom, 894 MHz is allocated for industrial applications, a frequency at which this invention is capable of operating. In North and South America, 915 MHz is allocated for unlimited use in industrial applications. Operation at 915 MHz is allowable in most parts of the world with proper screening and grounding to avoid interference with communications equipment.

Formerly, only low power magnetrons (<3 kW) were available for 2450 MHz use, but 15-60 kW magnetrons were available for 915 MHz use. Currently, magnetron selection from 2.2-60 kW exists at 2450 MHz, while magnetrons operating a 915 MHz are available from 10-200 kW. The preferred frequency of operation at 915 MHz for this invention was chosen primarily for increased penetration depth, increased power availability, increased operating efficiency, and longer operating life, resulting in a reduced number of magnetrons and lower cost per kilowatt of microwave output power.

Tuners

The tuners employed in the invention are either three- or four-stage tuners, preferably motor-driven with automatic feedback loops. When a manually tuned, three-stage microwave tuner assembly is employed, each tuning stub set (i.e., stubs 1 & 2 as well as sets 2 & 3) are separated by only ⅛ waveguide wavelengths. However, preferred is a four-stage automated tuner assembly. Increasing from a three-stage tuner assembly to a four-stage tuner more accurately matches the load/tuner combination, permitting the addition of automatic tuning for improved process operation. The automatic tuning assembly permits continuously-adjustable compensation to match the microwave generators to a changing load in the material within the applicator. Matching is achieved by controlling the amplitude of the reflection coefficient, while tandem or cascade movement controls the phase angle through a parameter known as susceptance. Susceptance within the waveguide section varies as the insertion depth and the selected diameter of the tuning slug, which results in controlling the amplitude of the reflection coefficient. For a four-stage tuner, stubs one 92 and three 96 control admittance, while stubs two 94 and four 98 control the conductance. Therefore, the reflection amplitude and phase angle can be varied with the tuner's adjustment range to achieve minimum net reflected power returning from the applicator. Tuning stubs 92 and 94 are separated by ¼ wavelength for optimum tuning effect. Tuning stubs 94 and 96 are separated by ⅜ waveguide wavelengths. Tuning stubs 96 and 98 are separated by ¼ waveguide wavelength. In this preferred embodiment, it is seen that there is an increased spatial distance between the first set of tuner stubs 92, 94 as compared to the second set of tuner stubs 96, 98, resulting in minimization (if not elimination) of interaction between the two sets of tuning stubs.

Diffuser Assemblies

The microwave diffuser matrix contributes significantly to the low reflected power, in that the maximum amount of applied power can be coupled directly into the preferred eight (8) diffuser modules per applicator through six (6) essentially parallel channels 90 per diffuser (illustrated with four assemblies in FIG. 13 and with a single assembly in exploded form in FIG. 14), each port having a curved or curvilinear bevel 90, for a total of forty-eight (48) applicator input channels in the diffuser matrix per applicator, with minimum losses and reflected power. The spacing between diffusor channels is between 1-2 waveguide wavelengths apart, more preferably approximately 1.5 waveguide wavelength. The spacing of each diffusor assembly is located waveguide wavelengths from each other and waveguide wavelengths to the applicator wall.

In this application, it should be noted that the number of channels per diffuser module is dependent on various factors which include applicator size, port cross-sectional area, and distance of separation between channels, to prevent arcing within diffuser channels. For a 60 kW microwave generator, four (4) channels are generally sufficient. For a 75 kW microwave generator, generally five (5) channels would be employed, while for a 100 kW microwave generator, six (6) channels would be used.

Power Density Control

One improvement is a shift in the understanding that process control is accomplished by power density control, instead of temperature or power control or simply by varying the belt speed. Power density is, by definition, power applied per unit volume of material. By shifting to power density control, it is possible to eliminate hot and cold spots within the entire length of the applicator, leading to greater uniformity and increased stabilization of the operation of the system as illustrated by the use of a directional coupler system, which monitors forward and reflected power.

The best mode for carrying out the invention has been described for purposes of illustrating the best mode known to the applicant at the time. The examples are illustrative only and not meant to limit the invention, as measured by the scope and merit of the claims. The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A process for reducing an organic-containing material into lower molecular weight gaseous hydrocarbons, liquid hydrocarbons and solid carbon constituents, said process comprising:

feeding a sample of said organic-containing material into an infeed system, wherein said infeed system contains a non-flammable blanketing purge gas;

transferring said material into at least one microwave applicator containing said purge gas in a pressurized state above local atmospheric pressure to insure that no air migrates into said microwave applicator which might cause a fire or explosion hazard;

exposing said material in said microwave applicator to at least two sources of microwaves from at least a pair of divaricated waveguide assemblies for a period of time sufficient to volumetrically reduce said material into said constituents, a frequency of said microwaves between approximately 894 MHz and approximately 1000 MHz and without an external heat source, said microwaves entering said at least one applicator being in non-parallel alignment to each other by using unequal lengths of waveguide between said sources of said microwaves and said at least one applicator;

said microwaves entering said at least one applicator through at least one applicator diffuser matrix for each divaricated waveguide, said matrix comprising at least four essentially parallel beveled entry channels; and collecting byproduct constituents from said organic-containing material.

2. The process of claim 1 wherein each of said applicator diffuser matrices comprise at least five beveled entry channels.

3. The process of claim 2 wherein each of said applicator diffuser matrices comprise at least six beveled entry channels.

4. The process of claim 1 wherein
said microwaves enter said at least one applicator through at least four applicator diffuser matrices, each of said matrices comprising at least four beveled entry channels.

5. The process of claim 4 wherein
said microwaves enter said at least one applicator through at least eight applicator diffuser matrices, each of said matrices comprising at least five beveled entry channels.

6. The process of claim 4 wherein
each of said at least four applicator diffuser matrices comprises at least six beveled entry channels.

7. The process of claim 5 wherein
each of said at least eight applicator diffuser matrices comprises at least six beveled entry channels.

8. The process of claim 1 which further comprises the step of:
monitoring a load in said organic-containing material within said at least one applicator and using at least one tuning stub to match a load/tuner combination.

9. The process of claim 1 wherein said step of monitoring comprises:
a four-stage automated tuner assembly having four tuner stubs, in which said tuning stubs match said load/tuner combination.

10. The process of claim 9 wherein,
said tuner stubs are motor-driven with individual feedback loops to a programmable logic controller assembly which provides continuously-adjustable compensation to match said source of said microwaves to a changing load in the organic-containing material within said at least one applicator.

11. The process of claim 10 wherein,
said step of matching is achieved by controlling an amplitude of a reflection coefficient of said organic-containing material by varying an insertion depth and a diameter of said tuning slug.

12. The process of claim 11 wherein,
a middle pair of tuning stubs are separated by ⅜ waveguide wavelength; and
each of an outer pair of tuning stubs are separated by ¼ waveguide wavelength.

13. An apparatus for reducing an organic-containing material into lower molecular weight gaseous hydrocarbons, liquid hydrocarbons and solid carbon constituents, which comprises:
at least one applicator chamber;
at least two sources of microwaves;
at least a pair of microwave waveguides of unequal length, each waveguide in communication with one of said at least two sources of microwaves and said applicator chamber; and
at least one applicator diffuser matrix at an entry port into said at least one applicator chamber from each of said at least said pair of microwave waveguides, said matrix comprising at least four beveled entry channels.

14. The apparatus of claim 13 which further comprises:
at least two pairs of microwave waveguides, each pair of waveguides being split into two by a divaricated waveguide assembly;
each divaricated waveguide assembly having at least one applicator diffuser matrix at said entry point into said at least one applicator chamber, said matrix comprising at least four essentially parallel beveled entry channels.

15. The apparatus of claim 14 wherein,
each of said matrices comprises at least five beveled entry channels.

16. The apparatus of claim 15 wherein,
each of said matrices comprises at least six beveled entry channels.

17. The apparatus of claim 13 wherein
said at least one applicator chamber is at least two applicator chambers in communication with each other;
said at least two sources of microwaves is at least four sources of microwaves;
at least two pair of microwave waveguides of unequal length, each waveguide in communication with a source of microwaves and said applicator chamber; and
at least one applicator diffuser matrix at an entry port into said at least one applicator chamber from each of said at least two pair of microwave waveguides, said matrix comprising at least four beveled entry channels.

18. The apparatus of claim 17 wherein said at least one applicator diffuser matrix comprises:
a sealed, dual-flanged waveguide isolation assembly between said microwave diffuser and said applicator input port which includes two low-loss, dielectric wafers inset within a flange of said isolation assembly.

19. The apparatus of claim 18 wherein
said waveguide isolation assembly is nitrogen-filled to maintain an inert, non-flammable atmosphere within said assembly.

20. The apparatus of claim 19 wherein
said at least one applicator is a sealed, purged low-loss seamless aluminum cavity.

21. A rectangular diffuser matrix positioned at an end of a waveguide which comprises:
at least four parallel beveled entry channels,
each of said beveled entry channels spaced apart by between 1 to 2 waveguide wavelengths.

22. The diffuser matrix of claim 21 which further comprises:
at least five parallel beveled entry channels.

23. The diffuser matrix of claim 22 which further comprises:
at least six parallel beveled entry channels.

24. The diffuser matrix of claim 21 which further comprises:
a sealed dual-flanged waveguide isolation assembly, wherein
said isolation assembly further comprises a pair of microwave-transparent windows.

25. The diffuser matrix of claim 24 wherein said microwave-transparent windows are a pair of dielectric wafers connected by a quarter-wavelength long section of waveguide.

26. The diffuser matrix of claim 25 wherein
said waveguide isolation assembly contains a non-flammable atmosphere.

* * * * *